US012678516B2

(12) United States Patent
Yin et al.

(10) Patent No.: US 12,678,516 B2
(45) Date of Patent: Jul. 14, 2026

(54) IMMUNOSTIMULATORY TOLL-LIKE RECEPTOR AGONIST-NANOPARTICLE FOR CANCER IMMUNOTHERAPY

(71) Applicant: The Board of Trustees of the Leland Stanford Junior University, Stanford, CA (US)

(72) Inventors: Qian Yin, Los Altos, CA (US); Mark M. Davis, Atherton, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 273 days.

(21) Appl. No.: 18/287,446

(22) PCT Filed: Apr. 20, 2022

(86) PCT No.: PCT/US2022/025494
§ 371 (c)(1),
(2) Date: Oct. 18, 2023

(87) PCT Pub. No.: WO2022/226032
PCT Pub. Date: Oct. 27, 2022

(65) Prior Publication Data

US 2024/0197910 A1 Jun. 20, 2024

Related U.S. Application Data

(60) Provisional application No. 63/287,333, filed on Dec. 8, 2021, provisional application No. 63/177,709, filed on Apr. 21, 2021.

(51) Int. Cl.

| | |
|---|---|
| ***A61K 47/69*** | (2017.01) |
| ***A61K 31/437*** | (2006.01) |
| ***A61K 45/06*** | (2006.01) |
| ***A61P 35/00*** | (2006.01) |
| ***A61P 37/04*** | (2006.01) |
| *B82Y 5/00* | (2011.01) |

(52) U.S. Cl.
CPC ........ *A61K 47/6937* (2017.08); *A61K 31/437* (2013.01); *A61K 45/06* (2013.01); *A61P 35/00* (2018.01); *A61P 37/04* (2018.01); *B82Y 5/00* (2013.01)

(58) Field of Classification Search
None
See application file for complete search history.

(56) References Cited

U.S. PATENT DOCUMENTS

| | | | | |
|---|---|---|---|---|
| 8,906,381 | B2 * | 12/2014 | Iannacone .............. | A61K 39/39 424/193.1 |
| 2010/0305300 | A1 | 12/2010 | Coulembier et al. | |
| 2012/0087890 | A1 | 4/2012 | Iannacone et al. | |
| 2015/0174268 | A1 | 6/2015 | Li | |
| 2020/0164090 | A1 | 5/2020 | Yin et al. | |
| 2021/0023208 | A1 * | 1/2021 | Seder ................. | A61K 48/0041 |

FOREIGN PATENT DOCUMENTS

| | | |
|---|---|---|
| WO | WO2010042863 | 4/2010 |
| WO | WO2010138194 | 12/2010 |

OTHER PUBLICATIONS

Kakwere et al., Advanced Healthcare Materials (2021), 10, 2100008 (15 pages).*

Patinote et al. (2020) "Agonist and antagonist ligands of toll-like receptors 7 and 8: Ingenious tools for therapeutic purposes." European journal of medicinal chemistry 193, 112238.

* cited by examiner

*Primary Examiner* — Brian J Davis
(74) *Attorney, Agent, or Firm* — Pamela J. Sherwood; Bozicevic, Field & Francis LLP

(57) ABSTRACT

Compositions and methods are provided relating to immunostimulatory TLR agonist nanoparticle formulations. Methods are provided for treating cancer, by stimulating an immune response to cancer cells through administering to an individual mammal an effective dose or series of doses of an immunostimulatory composition comprising an immunostimulatory TLR agonist-nanoparticle; optionally in combination with a second immune regulatory agent.

18 Claims, 11 Drawing Sheets

FIG. 1A
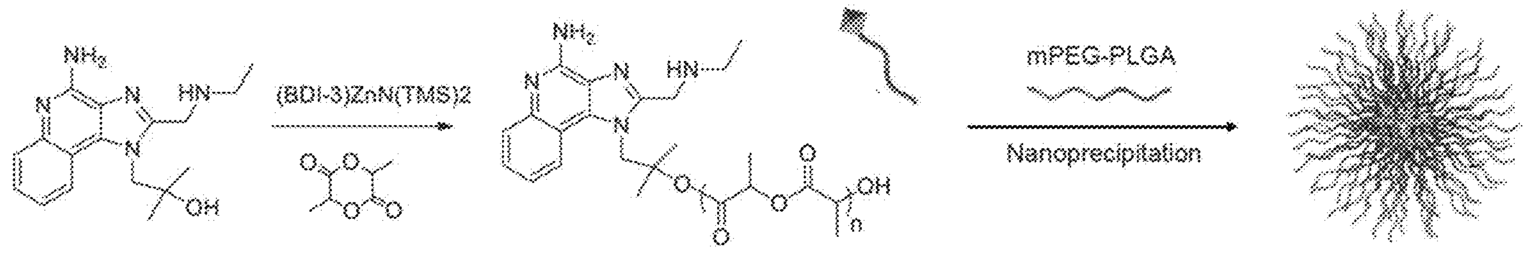
Initiator: gardiquimod
Monomer: lactide
Gardiquimod-polylactide (TLR7-PLA)
TLR7-NP
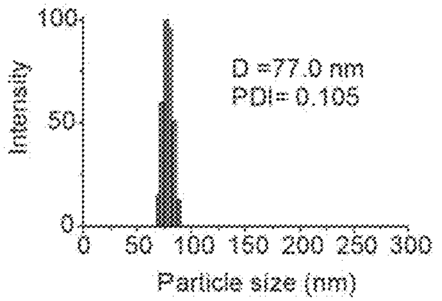
FIG. 1B
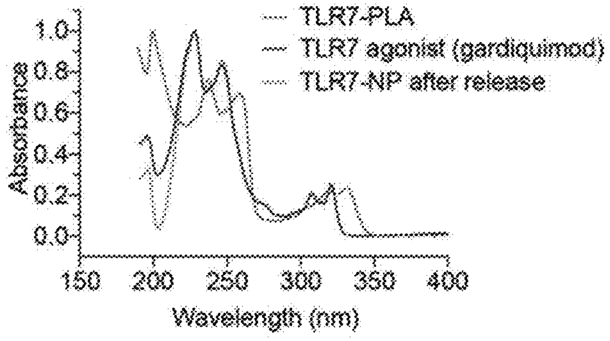
FIG. 1C
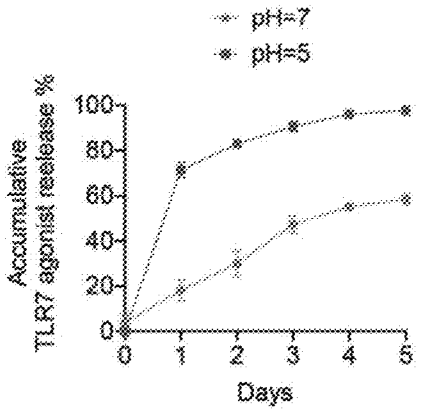
FIG. 1D FIG. 7A
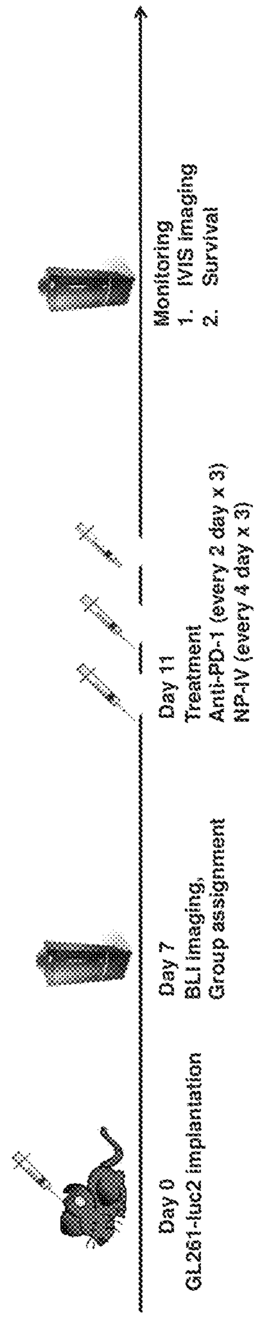
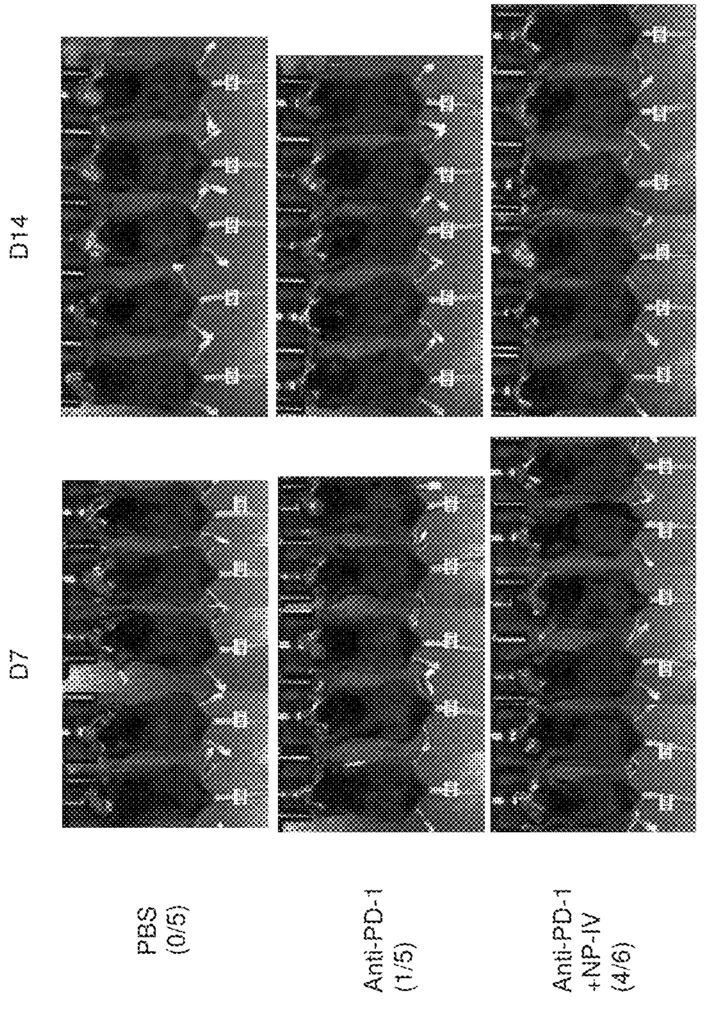
FIG. 7B

IMMUNOSTIMULATORY TOLL-LIKE RECEPTOR AGONIST-NANOPARTICLE FOR CANCER IMMUNOTHERAPY

CROSS REFERENCE TO RELATED APPLICATION

The present application claims the benefit of and priority to U.S. Provisional Patent Application No. 63/177,709 filed Apr. 21, 2021, and U.S. Provisional Patent Application No. 63/287,333 filed Dec. 8, 2021, the entire disclosure of which is hereby incorporated by reference in its entirety BACKGROUND Cancer immunotherapy, exemplified by immune checkpoint blockades, has held out the promise of harnessing a patient's own T cells to attack cancer cells. The immune system's natural capacity to detect and destroy abnormal cells may prevent the development of many cancers. However, cancer cells are sometimes able to avoid detection and destruction by the immune system. Cancer cells can reduce the expression of tumor antigens on their surface, making it harder for the immune system to detect them; express proteins on their surface that induce immune cell inactivation; and/or induce cells in the microenvironment to release substances that suppress immune responses and promote tumor cell proliferation and survival. Despite the clinical success of checkpoint inhibitors in certain cancer types, a significant percentage of patients (typically over 70%) don't respond to the treatment or have a recurrence. Thus, to develop new immunotherapeutic strategies that act alone and/or complement checkpoint blockades is clinically warranted.

Immune checkpoint proteins limit the strength and duration of immune responses. These proteins normally keep immune responses in check by preventing overly intense responses that might damage normal cells as well as abnormal cells. Blocking the activity of immune checkpoint proteins releases the "brakes" on the immune system, increasing its ability to destroy cancer cells. Immune checkpoint inhibitors in current clinical use include ipilimumab, which blocks the activity of CTLA4, which is expressed on the surface of activated cytotoxic T lymphocytes. CTLA4 acts as a "switch" to inactivate these T cells, thereby reducing the strength of immune responses; inhibiting it increases the cytotoxic T cell response. Two other FDA-approved checkpoint inhibitors, nivolumab and pembrolizumab work in a similar way, but they target PD-1.

Toll-like receptors (TLRs) are a class of pattern recognition receptors that play a bridging role in innate immunity and adaptive immunity. The activation of TLRs induces inflammatory responses and contributes to the development of antigen-specific anti-cancer immunity. TLR7, a member of TLR family, is an intracellular receptor expressed on the membrane of endosomes. TLR7 can be triggered not only by ssRNA during viral infections, but also by immune modifiers that share a similar structure to nucleosides. One example is imiquimod, a small molecular synthetic molecule acting as a TLR7 agonist. It has been approved by Food and Drug Administration (FDA) as a therapeutic agent for basal cell carcinoma and genital warts. Though it has aroused considerable clinical research interest and showed promising results in clinical studies, its clinical application has been hindered by undesired toxicities after systemic injection.

Developing a vaccine strategy capable of inducing robust anti-tumor immunity concurrent with minimal systemic side effects is crucial for the continued progress of TLR7 agonist-based cancer immunotherapies towards widespread clinical translation.

SUMMARY OF THE INVENTION

Immunostimulatory TLR agonist-nanoparticles are provided herein. The immunostimulatory nanoparticles comprise a TLR agonist conjugated to a polymer through cleavable linkages, which may be referred to herein as an "immunostimulatory nanoparticle". In some embodiments the cleavable linkage is ester linker. Other linkers include, for example, pH-sensitive amino ester linkers, redox-responsive disulfide linkers, etc. In some embodiments the polymer is polylactide (PLA). The polymer is formed into nanoparticles, from which the TLR agonist can be released in a sustained manner in vivo, thereby reducing undesirable toxicity associated with administration of the TLR agonist in a free form. Once internalized into cells, the release rate of the agonist from the nanoparticles is accelerated by the low pH in endosomes, leading to robust activation of intracellular TLR receptors, e.g. TLR7/8 receptors. In some embodiments the TLR agonist activates an endosomal TLR. In some embodiments the TLR agonist is a TLR7 agonist. In some embodiments the TLR agonist is a TLR8 agonist. In some embodiments the TLR agonist is gardiquimod.

In some embodiments the TLR agonist is conjugated to a polylactide (PLA) polymer through an ester linkage, where the conjugate has a structure:

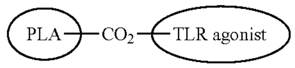

The number of lactide subunits in the polymer may range from about 5, about 10, about 15, up to about 100, up to about 50, up to about 30, up to about 25. In some embodiments, e.g. where the TLR agonist is gardiquimod, the conjugate has a structure:

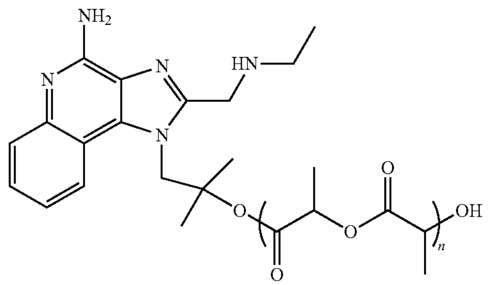

where n is from about 5 to 100.

The TLR agonist—polymer conjugate can self-assemble, or co-nanoprecipitate with a second polymer, to form biodegradable nanoparticles. In some embodiments the second polymer comprises polyethylene glycol (PEG) or a conjugate thereof. In some embodiments the second polymer comprises PEG conjugated to poly-lactic acid, poly-glycolic acid, or poly(lactic-co-glycolic acid). In some embodiments the second polymer is PEG-PLGA.

In some embodiments, methods are provided for treating cancer, by stimulating an immune response to cancer cells through administration of an immunostimulatory nanoparticle of the disclosure. The methods comprise administering to an individual mammal an effective dose or series of doses of an immunostimulatory composition comprising a TLR agonist-nanoparticle. In some embodiments the cancer is a solid tumor, e.g. carcinoma, glioma, melanoma, sarcoma, lymphoma, myeloma, etc. In some embodiments the cancer is a hematologic cancer. It is shown herein that the immunostimulatory effect of the nanoparticles does not require co-administration of a cancer-specific antigen, although a cancer-specific antigen may be optionally administered in combination with the immunostimulatory nanoparticle.

In some methods of treatment, the immunostimulatory nanoparticles are administered in combination with a second immune responsiveness modulator, e.g. an immune checkpoint inhibitor, an agonist of immune costimulatory molecules, etc. In some embodiments the immunostimulatory nanoparticles are administered in combination with an immune checkpoint inhibitor. In some embodiments the immune checkpoint inhibitor is an inhibitor of PD1 or PDL1. In some embodiments the immune checkpoint inhibitor is an inhibitor of CTLA4. In some embodiments a synergistic response is obtained by the combination of the immunostimulatory nanoparticles and an immune checkpoint inhibitor, as exemplified by a combination therapy with anti-PD1 agents.

In some embodiments, a cancer vaccine adjuvanted with an effective dose of a TLR agonist-nanoparticle of the disclosure is provided, comprising an effective dose of a cancer antigen. The antigen (immunogen) of interest may be co-precipitated with the polymers to form the immunostimulatory nanoparticle. The antigen may be conjugated to the nanoparticles. The antigen may be co-formulated with the nanoparticles in the absence of a physical linkage. Alternatively, the antigen can be adsorbed on alum and co-administrated with the nanoparticles. In some embodiments, a method of enhancing a recipient response to a vaccine is provided, where the vaccine comprises an effective dose of a TLR agonist-nanoparticle adjuvant of the disclosure. Advantages of the disclosed adjuvant include, for example, elicitation of B cell differentiation and antibody response to the vaccine with higher antigen-specific antibody-secreting cells (ASCs) in the bone marrow, combined with minimal systemic immune toxicity relative to, for example, free TLR agonist.

The effective dose of the adjuvant can be calculated, for example, by the dose of the TLR agonist that is provided in the nanoparticles, where an effective dose may be, from about a unit dose of 0.1 μg for an adult human recipient, from about 0.5 μg, from about 1 μg, from about 2 μg, from about 3 μg, from about 5 μg, from about 10 μg, from about 25 μg, up to about 1 mg, up to about 800 μg, up to about 600 μg, up to about 400 μg, up to about 200 μg, up to about 100 μg, up to about 50 μg.

In some embodiments, methods are provided for generating polymers comprising a plurality of ester linked TLR agonist moieties. In such methods, the TLR agonist, for example gardiquimod, is used as the initiator to initiate ring-opening polymerization (ROP) reaction of lactide to form a poly-lactide polymer comprising a defined level of agonist loading. The agonist may be from about 5% to about 25% wt. % of the polymer, e.g. from about 7.5% to about 20%, from about 10% to about 17.5%, from about 12.5% to about 15%. This method provides for quantitative incorporation of the agonist into PLA polymers, with precisely controlled composition and molecular weights.

The TLR agonist conjugated polymer is able to self-assemble, or co-nanoprecipitate with a second polymer, to form biodegradable nanoparticles. In some embodiments the second polymer comprises polyethylene glycol (PEG) or a conjugate thereof. In some embodiments the second polymer comprises PEG conjugated to poly-lactic acid, polyglycolic acid, or poly(lactic-co-glycolic acid). In some embodiments the second polymer is PEG-PLGA.

In some embodiments the immunostimulatory composition comprises a biodegradable nanoparticle from about 10 nm in diameter to about 100 nm in diameter, and may be from about 25 nm to about 100 nm in diameter, from about 50 to about 100 nm, from about 75 nm in diameter to about 100 nm in diameter, from about 60 nm to about 85 nm in diameter. A narrow size distribution can be achieved, where the standard deviation of diameter is less than about 25 nm, less than about 15 nm, less than about 10 nm. The size of nanoparticles can be tuned by changing the organic solvents in which the TLR agonist conjugated polymer is dissolved to generate larger particles, e.g. from about 100 nm up to about 1 μm; up to about 750 nm, up to about 500 nm, up to about 250 nm.

Other aspects and features will be readily apparent to the ordinarily skilled artisan upon reading the present disclosure.

BRIEF DESCRIPTION OF THE DRAWINGS

The invention is best understood from the following detailed description of exemplary embodiments when read in conjunction with the accompanying drawings. It is emphasized that, according to common practice, the various features of the drawings are not necessarily to-scale. On the contrary, the dimensions of the various features are arbitrarily expanded or reduced for clarity. Included in the drawings are the following figures:

FIG. 1A-1D. Synthesis, formulation, and characterization of gardiquimod-polylactide nanoparticles (TLR7-NP). (a) Schematic illustration of synthesizing TLR7-PLA polymer conjugate via gardiquimod initiated ring-opening polymerization of lactide and preparing TLR7-NPs through nanoprecipitation. (b) Hydrodynamic sizes of TLR7-NPs characterized by DLS analysis. (c) The UV absorbance of TLR7-PLA polymer, TLR7 agonist (gardiquimod), and TLR7-NPs after release measured by UV spectrometer at $\lambda$=321 nm. (d) Release kinetic profile of TLR7 agonist (gardiquimod) from TLR7-NPs in PBS buffer at pH 5.0 and pH 7.4.

FIG. 7A-7B. Intravenous injection of TLR7-NPs shows synergistic effect with anti-PD-1 in orthotropic GBM, (a) Study regimen and timeline. (b) Luminescent imaging of tumor burden of mice on day 7 (pre-treatment) and day 14 (7 days post treatment of PBS, anti-PD-1 alone, and TLR7-NPs plus anti-PD-1).

DETAILED DESCRIPTION OF THE EMBODIMENTS

Figure 2A:
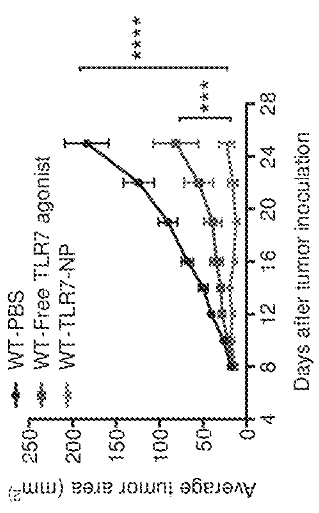
FIG. 2A-2D. TLR7-NPs outperform free TLR7 agonist in suppressing tumor growth, prolonging overall survival, and establishing protective memory in MC38 colon cancer model. C57BL/6 mice were inoculated subcutaneously with $5\times10^5$ MC38 tumor cells and treated with PBS, free TLR7 agonist and TLR7-NPs, respectively on days 8, 11, and 14. Average and individual MC38 tumor growth curves are shown in (a) and (b). * $p<0.001$;  $p<0.0001$ analyzed by two-way ANOVA. (c) The percentage survival of mice bearing the MC38 tumors after three treatments was monitored over time. n.s. no statistical significance; , $p<0.01$. Data was analyzed by Log-rank (Mantel-Cox) test. (d) The percentage survival of mice survivors after tumor rechallenge on day 70.

It is to be understood that the invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the polypeptide" includes reference to one or more polypeptides and equivalents thereof known to those skilled in the art, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As used herein, compounds which are "commercially available" may be obtained from commercial sources including but not limited to Acros Organics (Pittsburgh PA), Aldrich Chemical (Milwaukee WI, including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester PA), Crescent Chemical Co. (Hauppauge NY), Eastman Organic Chemicals, Eastman Kodak Company (Rochester NY), Fisher Scientific Co. (Pittsburgh PA), Fisons Chemicals (Leicestershire UK), Frontier Scientific (Logan UT), ICN Biomedicals, Inc. (Costa Mesa CA), Key Organics (Cornwall U.K.), Lancaster Synthesis (Windham NH), Maybridge Chemical Co. Ltd. (Cornwall U.K.), Parish Chemical Co. (Orem UT), Pfaltz & Bauer, Inc. (Waterbury CN), Polyorganix (Houston TX), Pierce Chemical Co. (Rockford IL), Riedel de Haen AG (Hannover, Germany), Spectrum Quality Product, Inc. (New Brunswick, NJ), TCI America (Portland OR), Trans World Chemicals, Inc. (Rockville MD), Wako Chemicals USA, Inc. (Richmond VA), Novabiochem and Argonaut Technology.

Compounds useful for co-administration with the active agents of the invention can also be made by methods known to one of ordinary skill in the art. As used herein, "methods known to one of ordinary skill in the art" may be identified through various reference books and databases. Suitable reference books and treatises that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C. may be contacted for more details). Chemicals that are known but not commercially available in catalogs may be prepared by custom chemical synthesis houses, where many of the standard chemical supply houses (e.g., those listed above) provide custom synthesis services.

The term "immunostimulatory" as used herein, is meant a composition that induces cellular or humoral immune responses. In the methods disclosed herein, an immune response to endogenous cancer cells is generated. Administration of exogenous antigen is not required for the therapeutic response, although optionally a tumor-specific antigen can be administered with the nanoparticles. An immunostimulatory adjuvant, or immunostimulatory nanoparticles according to the disclosure herein, comprise a TLR agonist nanoparticle adjuvant generated by using a TLR agonist, for example gardiquimod, as an initiator to initiate ring-opening polymerization (ROP) reaction of lactide to form a poly-lactide polymer comprising a defined level of agonist loading.

Some embodiments of the invention provide a method of stimulating an immune response in a mammal, which can be a human or a preclinical model for human disease, e.g. mouse, ape, monkey etc., particularly stimulating an immune response against endogenous cancer cells. "Stimulating an immune response" includes, but is not limited to, inducing a therapeutic or prophylactic effect that is mediated by the immune system of the mammal. More specifically, stimulating an immune response in the context of the invention refers to eliciting cellular or humoral immune responses, thereby inducing downstream effects including, without limitation, one or more of production of antibodies, antibody heavy chain class switching, maturation of APCs, and stimulation of cytolytic T cells, T helper cells and both T and B memory cells.

The term "immune response" and grammatical equivalents refer to a response by the immune system of a subject. For example, immune responses include, but are not limited to, a detectable alteration, e.g., increase, in Toll-like receptor (TLR) activation; lymphokine, e.g., Th1 or Th2 type cytokines, or chemokine, expression and/or secretion; macrophage activation; dendritic cell activation; T cell activation, e.g., CD4+ or CD8+ T cells; NK cell activation; and/or B cell activation, e.g., antibody generation and/or secretion. Additional examples of immune responses include binding of an immunogen to an MHC molecule and inducing a cytotoxic T lymphocyte response; inducing a B cell response, e.g., antibody production; and/or T-helper lymphocyte response; and/or a delayed type hypersensitivity (DTH) response against the antigen from which the immunogenic polypeptide is derived; expansion of cells of the immune system; and increased processing and presentation of antigen by antigen presenting cells.

An immune response may be to immunogens that the subject's immune system recognizes as foreign, e.g., neoantigens, tumor-specific antigens, self-antigens recognized as foreign, etc. Thus, it is to be understood that, as used herein, "immune response" refers to any type of immune response, including, but not limited to, innate immune responses, cell-mediated immune responses, and humoral immune responses. The term "immune response" is meant to encompass all aspects of the capability of a subject's immune system to respond to antigens and/or immunogens including the initial response to an immunogen as well as acquired, e.g., memory, responses that are a result of an adaptive immune response.

Some embodiments of the invention provide a method of stimulating an immune response in a mammal, which can be a human or a preclinical model for human disease, e.g. mouse, ape, monkey etc. "Stimulating an immune response" includes, but is not limited to, inducing a therapeutic or prophylactic effect that is mediated by the immune system of the mammal. More specifically, stimulating an immune response in the context of the invention refers to eliciting cellular or humoral immune responses, thereby inducing downstream effects such as production of antibodies, antibody heavy chain class switching, maturation of APCs, and stimulation of cytolytic T cells, T helper cells and both T and B memory cells.

The terms "humoral immunity" and "humoral immune response" refer to the form of immunity in which antibody molecules are produced in response to antigenic stimulation.

The terms "cell-mediated immunity" and "cell-mediated immune response" are meant to refer to the immunological defense provided by lymphocytes, such as that defense provided by T cell lymphocytes when they come into close proximity to their victim cells. A cell-mediated immune response normally includes lymphocyte proliferation. When "lymphocyte proliferation" is measured, the ability of lymphocytes to proliferate in response to a specific antigen is measured. Lymphocyte proliferation is meant to refer to B cell, T-helper cell or cytotoxic T-lymphocyte (CTL) cell proliferation.

As used herein, the term "a composition for inducing an immune response" refers to a composition, e.g. an immunostimulatory composition of the disclosure, that, once administered to a subject, e.g., once, twice, three times or more, separated by a period of time, e.g. weeks, months or years, stimulates, generates and/or elicits an immune response in the subject resulting in total or partial response to a tumor. While not required, in some embodiments of the invention, the composition comprises one or more antigens/immunogens together with the immunostimulatory composition, providing adjuvant activity, formulated for administration, e.g., via injectable route such as intradermal, intramuscular, subcutaneously, intravenously, etc., mucosal route, e.g., nasally or vaginally, or other route to a subject. In further embodiments, the immunogenic composition comprises one or more other compounds or agents including, but not limited to, therapeutic agents, physiologically tolerable liquids, gels, carriers, diluents, adjuvants, excipients, salicylates, steroids, immunosuppressants, immunostimulants, antibodies, cytokines, antibiotics, binders, fillers, preservatives, stabilizing agents, emulsifiers, and/or buffers.

The term "eliciting an immune response" is used herein generally to encompass induction and/or potentiation of an immune response. The term "inducing an immune response" refers to an immune response that is stimulated, initiated, or induced. The term "potentiating an immune response" refers to a pre-existing immune response that is improved, furthered, supplemented, amplified, enhanced, increased or prolonged.

The expression "enhanced immune response" or similar means that the immune response is elevated, improved or enhanced to the benefit of the host relative to the prior immune response status, for example, before the administration of a composition of the invention, or in the absence of an adjuvant of the disclosure.

The term "immunogenic amount" refers to an amount of a composition sufficient to stimulate an immune response, when administered with a subject immunogenic composition, as compared with the immune response elicited by the antigen in the absence of the polynucleotide adjuvant.

The term "effective dose" or "effective dosage" is defined as an amount sufficient to achieve or at least partially achieve the desired effect. The term "therapeutically effective dose" is defined as an amount sufficient to induce an immune response to the antigen and may at least at least partially arrest an infectious disease and its complications in a patient already suffering from the disease. Amounts effective for this use will depend upon the severity of the disorder being treated and the general state of the patient's own immune system.

The term "an amount effective to induce an immune response" of a composition for inducing an immune response comprising a nanoparticle adjuvant formulated for administration, refers to the dosage level required when administered to a subject to stimulate, generate and/or elicit an immune response in the subject. An effective amount can be administered in one or more administrations via the same or different route, applications or dosages and is not intended to be limited to a particular formulation or administration route. Accordingly, a "therapeutically effective amount" or "effective dose" of a composition for inducing an immune response refers to the dosage level or amount of a composition required when administered to a subject to stimulate, generate and/or elicit a therapeutic benefit in a subject. A therapeutically effective amount can be administered in one or more administrations, via the same or different route, applications or dosages and is not intended to be limited to a particular formulation or administration route.

The expression "enhanced immune response" or similar means that the immune response is elevated, improved or enhanced to the benefit of the host relative to the prior immune response status, for example, before the administration of an immunogenic composition of the invention.

The terms "humoral immunity" and "humoral immune response" refer to the form of immunity in which antibody molecules are produced in response to antigenic stimulation.

The terms "cell-mediated immunity" and "cell-mediated immune response" are meant to refer to the immunological defense provided by lymphocytes, such as that defense provided by T cell lymphocytes or natural killer cells when they come into close proximity to their target cells. A cell-mediated immune response normally includes lymphocyte proliferation. When "lymphocyte proliferation" is measured, the ability of lymphocytes to proliferate in response to a specific antigen is measured. Lymphocyte proliferation is meant to refer to B cell, T-helper cell or cytotoxic T-lymphocyte (CTL) cell proliferation.

The term "immunogenic amount" refers to an amount of an agent sufficient to stimulate an immune response.

The term "effective dose" or "effective dosage" is defined as an amount sufficient to achieve or at least partially achieve the desired effect. The term "therapeutically effective dose" is defined as an amount sufficient to induce an immune response to the antigen and may at least at least partially arrest cancer and its complications in a patient already suffering from the disease. Amounts effective for this use will depend upon the severity of the disorder being treated and the general state of the patient's own immune system.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

The terms "subject" and "patient" are used interchangeably herein to mean a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of interest. As will be evidence from the context in which the term is used, subject and patient refer to a subject or patient with cancer.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

As used herein, endpoints for treatment will be given a meaning as known in the art and as used by the Food and Drug Administration.

Overall survival is defined as the time from randomization until death from any cause, and is measured in the intent-to-treat population. Survival is considered the most reliable cancer endpoint, and when studies can be conducted to adequately assess survival, it is usually the preferred endpoint. This endpoint is precise and easy to measure, documented by the date of death. Bias is not a factor in endpoint measurement. Survival improvement should be analyzed as a risk-benefit analysis to assess clinical benefit. Overall survival can be evaluated in randomized controlled studies. Demonstration of a statistically significant improvement in overall survival can be considered to be clinically significant if the toxicity profile is acceptable, and has often supported new drug approval. A benefit of the methods of the invention can include increased overall survival of patients.

Endpoints that are based on tumor assessments include DFS, ORR, TTP, PFS, and time-to-treatment failure (TTF). The collection and analysis of data on these time-dependent endpoints are based on indirect assessments, calculations, and estimates (e.g., tumor measurements). Disease-Free Survival (DFS) is defined as the time from randomization until recurrence of tumor or death from any cause. The most frequent use of this endpoint is in the adjuvant setting after definitive surgery or radiotherapy. DFS also can be an important endpoint when a large percentage of patients achieve complete responses with chemotherapy.

Objective Response Rate. ORR is defined as the proportion of patients with tumor size reduction of a predefined amount and for a minimum time period. Response duration usually is measured from the time of initial response until documented tumor progression. Generally, the FDA has defined ORR as the sum of partial responses plus complete responses. When defined in this manner, ORR is a direct measure of drug antitumor activity, which can be evaluated in a single-arm study.

Time to Progression and Progression-Free Survival. TTP and PFS have served as primary endpoints for drug approval. TTP is defined as the time from randomization until objective tumor progression; TTP does not include deaths. PFS is defined as the time from randomization until objective tumor progression or death. The precise definition of tumor progression is important and should be carefully detailed in the protocol.

"In combination with", "combination therapy" and "combination products" refer, in certain embodiments, to the concurrent administration to a patient of the agents described herein. When administered in combination, each component can be administered at the same time or sequentially in any order at different points in time. Thus, each component can be administered separately but sufficiently closely in time so as to provide the desired therapeutic effect.

"Concomitant administration" of active agents in the methods of the invention means administration with the reagents at such time that the agents will have a therapeutic effect at the same time. Such concomitant administration may involve concurrent (i.e. at the same time), prior, or subsequent administration of the agents. A person of ordinary skill in the art would have no difficulty determining the appropriate timing, sequence and dosages of administration for particular drugs and compositions of the present invention.

As appreciated by skilled artisans, immunostimulatory compositions are suitably formulated to be compatible with the intended route of administration, e.g. intra-tumoral injection, parenteral administration, etc. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH of the composition can be adjusted with acids or bases, such as hydrochloric acid or sodium hydroxide. Systemic administration of the composition is also suitably accomplished by transmucosal or transdermal means. For transmucosal or transdermal administration, for example in the treatment of skin cancers, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories.

Immunostimulatory compositions may include an aqueous medium, pharmaceutically acceptable inert excipient such as lactose, starch, calcium carbonate, and sodium citrate. Immunostimulatory compositions may also include an adjuvant, for example Freud's adjuvant. The immunostimulatory nanoparticles may be administered alone or in combination with a physiologically acceptable vehicle that is suitable for administration to humans. Immunostimulatory nanoparticles may be delivered intra-tumorally, orally, parenterally, intramuscularly, intranasally, intravenously, transdermally, etc. Oral delivery may encompass, for example, adding the compositions to the feed or drink of the mammals. Factors bearing on the immunostimulatory nanoparticle dosage include, for example, the weight and age of the mammal. Compositions for parenteral or intravenous delivery may also include emulsifying or suspending agents or diluents to control the delivery and dose amount of the immunostimulatory nanoparticles.

"Polypeptide" and "protein" as used interchangeably herein, can encompass peptides and oligopeptides. Where "polypeptide" is recited herein to refer to an amino acid sequence of a naturally-occurring protein molecule, "polypeptide" and like terms are not necessarily limited to the amino acid sequence to the complete, native amino acid sequence associated with the recited protein molecule, but instead can encompass biologically active variants or fragments, including polypeptides having substantial sequence similarity or sequence identify relative to reference amino acid sequences. In general, fragments or variants retain a biological activity of the parent polypeptide from which their sequence is derived. Polypeptides may be, for example, at least 8 amino acids in length, at least 10, at least 12, at least 14, at least 16, at least 18, at least 20, at least 22, at least 24, and may be at least 30, at least 40, at least 50, at least 75, at least 100 or more amino acids in length.

Polypeptides suitable can be obtained from any species, e.g., mammalian or non-mammalian (e.g., reptiles, amphibians, avian (e.g., chicken)), particularly mammalian, including human, rodent (e.g., murine or rat), bovine, ovine, porcine, murine, or equine, particularly rat or human, from any source whether natural, synthetic, semi-synthetic or recombinant. In general, polypeptides comprising a sequence of a human polypeptide are of interest.

The term "derived from" indicates molecule that is obtained directly from the indicated source (e.g., when a protein directly purified from a cell, the protein is "derived from" the cell) or information is obtained from the source, e.g. nucleotide or amino acid sequence, from which the molecule can be synthesized from materials other than the source of information.

The term "isolated" indicates that the recited material (e.g, polypeptide, nucleic acid, etc.) is substantially separated from, or enriched relative to, other materials with which it occurs in nature (e.g., in a cell). A material (e.g., polypeptide, nucleic acid, etc.) that is isolated constitutes up to about 0.1%, up to about 0.5%, up to about 1% or up to about 5% by weight of the total material of the same type (e.g., total protein, total nucleic acid) in a given sample.

The term "unit dosage form," as used herein, refers to physically discrete units suitable as unitary dosages for human and animal subjects, each unit containing a predetermined quantity of compounds calculated in an amount sufficient to produce the desired effect in association with a pharmaceutically acceptable diluent, carrier or vehicle. The specifications for the novel unit dosage forms depend on the particular compound employed and the effect to be achieved, and the pharmacodynamics associated with each compound in the host.

A "pharmaceutically acceptable excipient", "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and is usually free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including intra-tumoral, transdermal, oral, buccal, rectal, parenteral, intraperitoneal, intradermal, intracheal and the like.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three-dimensional structural characteristics, as well as specific charge characteristics.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Each mAb is directed against a single determinant on the antigen. In addition to their specificity, the monoclonal antibodies are advantageous in that they can be synthesized by cell culture, uncontaminated by other immunoglobulins. The modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made in an immortalized B cell or hybridoma thereof, may be made by recombinant DNA methods, including without limitation yeast display.

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix, e.g. a particle, to which the immunostimulatory components can adhere, be conjugated to, or be encapsulated within.

An "effective amount of an antigenic compound" refers to an amount of antigenic compound which, in optional combination with an immunostimulatory nanoparticle, will cause the subject to produce a specific immunological response to the antigenic compound.

Adjuvants and TLR Agonists

The term "adjuvant" or "immunostimulatory adjuvant" as used herein refers to a substance or combination of substances that non-specifically enhances the immune response to an antigen, including endogenous antigens such as cancer cells, and in particular the TLR agonist nanoparticle adjuvants disclosed herein. Adjuvants are effective in stimulating immunity.

The innate immunity system comprises several families of pattern recognition receptors (PPRs). The latter receptors serve to identify pathogen-associated molecular patterns (PAMPs) and danger-associated molecular patterns (DAMPs). The PPRs act as the primary defense against pathogenic entities and control the activation and progression of the adaptive immunity by activating the production not only of pro-inflammatory cytokines, chemokines and interferons, but also B and T cells. Among the PPRs, the Toll-like Receptors (TLRs) are of interest.

TLRs are divided into two groups depending on their subcellular localization, which largely correlate with the type of molecular patterns they are able to recognize. Among endosomal TLRs, TLR7 and TLR8 have a high degree of sequence homology and function similarity. Both receptors recognize viral single-stranded RNAs, as well as synthetic tricyclic derivatives belonging to the imidazo[4,5-c]quinoline series, including without limitation resiquimod, a TLR7/8 agonist.

TLR7, TLR8 and TLR9 induce antiviral responses by the production of IFNα as well as pro-inflammatory cytokines. These three receptors use the MyD88 adapter protein to initiate the signaling pathways. The IRF7 transcription factor (Interferon regulatory factor 7) is responsible for the expression and production of IFNα. MyD88 interacts directly with IRF7 at the endosome. IRF7 also interacts with TRAF6, another adapter molecule that operates downstream of MyD88, and after receptor activation (TLRs 7, 8 or 9), IRF7 is activated in a MyD88 and TRAF6 dependent manner.

TLR7 and TLR8 together mediate recognition of purine-rich ssRNA to elicit an immune response to pathogens recognized in the endosome. TLRs 7 and 8 are implicated in the recognition of naturally derived uridine-rich ssRNAs of influenza and HIV. In addition TLR7 and TLR8 recognize bacterial RNA. Furthermore, TLR7 and 8 are expressed in human plasmacytoid DCs (pDCs), in T and B cells, monocytes and macrophages. Naive human B cells express low levels of TLR7 and, whereas activated and memory human B cells also express a broader range of TLRs including TLR7. B cell intrinsic TLR7 signaling may play a role in B cell responses during chronic infections which could be used to activate memory B cells and boost humoral immune responses during immunization. Synthetic small molecules agonists that activate TLRs 7 and 8 are useful as adjuvants in the formulations described herein.

For a review of TLR7/8 agonists, see, for example, Patinote et al. (2020) Eur J Med Chem. 193:112238, herein specifically incorporated by reference. Examples of agonists include, without limitation, Bropirimine (2-amino-5-bromo-6-phenylpyrimidin-4-ol); N-4-butyl-6-methyl-5-(3-morpholinopropyl)-pyrimidine-2,4-diamine with simultaneous TLR7 and TLR8 agonist activities; 1-pentyl-4-phenyl-1H-imidazol-2-amine; SM-360320 is a TLR7 agonist; SM-276001 is a selective and potent TLR7 agonist; TMX-202 is a second-generation SM-360320 prodrug, which conjugates the TLR7 ligand to a C12 phospholipid via a benzoic acid functional group. TMX-302 and TMX-306 are PEGylated SM-360320 purine-like compounds characterized by TLR7 partial agonist activity; SZU-101; CL264 is a TLR7 specific agonist; CL307 links a spermine to CL264; AdiFectin™ (CL347); Adilipoline™ (CL413) is a derivative obtained by linearly linking a hydroxyadenine derivative with the terminal acid function of Pam2CSK4; CL531 corresponds to the conjugation of a hydroxyadenine derivative to the lateral chain of the second lysine of Pam2CSK4; CL572 contains a monoacyl-ethyl-cystein group grafted to a hydroxyadenine via a glutamic acid derivative; DSR-6434 is a specific TLR7 agonist; DSR-29133 is a TLR7-selective agonist; loxoribine and isatoribine activate immune cells exclusively via TLR7; Selgantolimod; SC1 (Pluripotin) is a TLR7 agonist; VTX-2337 (also known as Motolimod) is a selective and potent agonist of TLR 8; VTX-294 is a potent TLR8 agonist; VTX-763 is a TLR8 agonist; VTX-463 is a dual TLRs 7/8 agonist; TL8-506 is a TLR8 ligand; Imiquimod is a tricyclic nitrogen molecule belonging to the imidazo[4,5-c]quinoline series activating TLR7; Resiquimod is an imidazo[4,5-c]quinoline compound that activates TLR7 and TLR8; CL097 is TLR7 and TLR8 agonist; Compound 3M-001; 3M-002; Compound 3M-003 and 3M-011 are an agonist of both TLR7 and TLR8; Telratolimod is a TLR7/8 agonist; Gardiquimod is an agonist of TLR7 but not of human TLR8; LHC165 is a TLR7 agonist; MCT465 is a high molecular weight synthetic double-stranded RNA (dsRNA) that activates TLRs 3/7/8 signaling; CV8102 is a ssRNA-based TLRs 7/8 agonist.

CL413, CL531, selgantolimod, resiquimod, gradiquimod, and 3M-003 can be directly used for initiation of ring-opening polymerization as disclosed herein. Other agonists as described above can be chemically modified with the introduction of hydroxyl group on the side chain to be compatible with this method.

The dose of agonist present in a unit dose of the immunostimulatory nanoparticles may be within current clinical practice, for example CL413 at 50 μg-10 μg/ml (~30 pM-10 μM) for a human unit dose; CL531 at 5 μg-10 μg/ml (~3 pM-10 μM) for a human unit dose; Selgantolimod up to 3 mg per dose; Resiquimod from 10 ng-10 μg/ml with clinical trials of up to 0.02 mg/kg; Gardiquimod from 0.1-3 μg/ml in a unit dose.

Useful agonists in clinical trials include, for example:

| Ligand | TLR | Clinical Trial Identification |
|---|---|---|
| 852A (PF-04878691, S-32865 3M852A) | 7 | NCT00319748 |
| Imiquimod, R837 | 7 | NCT00453050 |
| Resiquimod, R848 | 7/8 | NCT01737580 |
| AZD8848, DSP-3025, AZD-3025 | 7 | NCT01124396 |
| GSK2245035 | 7 | NCT01607372 |
| GS-9620 vesatolimod | 7 | NCT02166047 |
| RO7020531 | 7 | NCT03530917 |
| RO6864018 (ANA773, ANA773, RG7795) | 7 | NCT02015715 |
| RO6871765 or RO7011785 | 7 | NCT02498275 |
| DSP-0509 | 7 | NCT03416335 |
| NJH395 | 7 | NCT03696771 |
| BNT411 | 7 | NCT04101357 |
| TQ-A3334, JNJ-4964, AL-034 | 7 | NCT04180150 |
| LHC165 | 7 | NCT03301896 |

-continued

| Ligand | TLR | Clinical Trial Identification |
|---|---|---|
| Hydroxychloroquine | 7/9 | NCT01601028 |
| MEDI9197 | 7/8 | NCT02556463 |
| NKTR-262 | 7/8 | NCT03435640 |
| CV8102 | 7/8 | NCT03203005 |
| VTX-2337, Motolimod | 8 | NCT01334177 |
| VTX-2337 | 8 | NCT03906526 |
| GS-9688 | 8 | NCT03615066 |

Immunostimulatory Nanoparticles

Immunostimulatory nanoparticles are comprised of polymers comprising a plurality of ester linked TLR agonist moieties. A TLR agonist as described above, for example gardiquimod, is used as the initiator to initiate ring-opening polymerization (ROP) reaction of lactide to form a polylactide polymer comprising a defined level of agonist loading. The agonist may be from about 5% to about 25% wt. % of the polymer, e.g. from about 7.5% to about 20%, from about 10% to about 17.5%, from about 12.5% to about 15%. This method provides for quantitative incorporation of the agonist into PLA polymers, with precisely controlled composition and molecular weights.

The TLR agonist conjugated polymer is able to self-assemble, or co-nanoprecipitate with a second polymer, to form biodegradable nanoparticles. In some embodiments the second polymer comprises polyethylene glycol (PEG) or a conjugate thereof. In some embodiments the second polymer comprises PEG conjugated to poly-lactic acid, polyglycolic acid, or poly(lactic-co-glycolic acid). In some embodiments the second polymer is PEG-PLGA. The ratio of PEG-PLGA to TLR agonist conjugated polymer can be selected to optimize the dose of TLR agonist that the provided, for example the ratio (wt/wt) can range from about 100:1 PEG-PLGA to TLR agonist conjugated polymer to about 1:100, including ranges from about 50:1; 25:1, 10:1, 5:1, 3:1, 2:1, 1:1, 1:2, 1:3, 1:5, 1:10, 1:25, 1:50, and intervening ratios.

In some embodiments a nanoparticle is a biodegradable nanoparticle from about 10 nm in diameter to about 100 nm in diameter, and may be from about 25 nm to about 100 nm in diameter, from about 50 to about 100 nm, from about 75 nm in diameter to about 100 nm in diameter, from about 60 nm to about 85 nm in diameter. A narrow size distribution can be achieved, where the standard deviation of diameter is less than about 25 nm, less than about 15 nm, less than about 10 nm. The size of nanoparticles can be tuned by changing the organic solvents in which the TLR agonist conjugated polymer is dissolved to generate larger particles, e.g. from about 100 nm up to about 1 μm; up to about 750 nm, up to about 500 nm, up to about 250 nm.

Nanoparticles disclosed herein are formed from materials that are biodegradable and non-toxic. The optional antigen, if present, may be dispersed or encapsulated within the nanoparticle, linked to the nanoparticle, or formulated with the nanoparticle in the absence of physical linkage.

Biodegradable polymers particularly preferred in the present invention include polylactides (PLA), polyglycolides (PGA), poly(lactide-co-glycolides) (PLGA), polyanhydrides, polycaprolactone, poly-3-hydroxybutyrate and polyorthoesters. Such biodegradable polymers have been characterized extensively and can be formulated to exhibit desired degradation properties as (see, e.g., Edlund & Albertsson, Degradable Aliphatic Polyesters, pp. 67-112 (2002), Barman et al., J. of Controlled Release 69:337-344

(2000); Cohen et al., Pharmaceutical Res. (8): 713-720 (1991)). Degradation and drug release kinetics can be precisely controlled by the physicochemical properties of the polymer, such as molecular weight, dispersity index, hydrophobicity, and crystallinity.

In one particular embodiment, the polymer comprises poly(lactide-co-glycolides) (PLGA)-PEG. PLGA is a copolymer which has been used in a host of FDA approved therapeutic devices, owing to its biodegradability and biocompatibility. During polymerization, successive monomeric units of glycolic or lactic acid are linked together in PLGA by ester linkages, thus yielding a linear, aliphatic polyester as a product.

Depending on the ratio of lactide to glycolide used for the polymerization, different forms of PLGA can be obtained: these are usually identified in regard to the monomers' ratio used (e.g., PLGA 75:25 identifies a copolymer whose composition is 75% lactic acid and 25% glycolic acid). PLGA degrades by hydrolysis of its ester linkages in the presence of water. It has been shown that the time required for degradation of PLGA is related to the monomers' ratio used in production: the higher the content of glycolide units, the lower the time required for degradation. An exception to this rule is the copolymer with 50:50 monomer ratio which exhibits a faster degradation (about two months). In addition, polymers that are end-capped with esters (as opposed to the free carboxylic acid) demonstrate longer degradation half-lives.

Antigens

As used herein, the term "antigenic compound" refers to any substance that can be recognized by the immune system (e.g., bound by an antibody or processed so as to elicit a cellular immune response) under appropriate conditions. In some embodiments, an exogenous antigenic compound is not administered with the immunostimulatory nanoparticles. In other embodiments, an optional tumor-associated antigen is administered in a combination therapy.

An "antigen" as used herein includes but is not limited to cells; cell extracts; proteins; lipoproteins; glycoproteins; nucleoproteins; polypeptides; peptides; polysaccharides; polysaccharide conjugates; peptide mimics of polysaccharides; lipids; glycolipids; carbohydrates; etc. In some embodiments of the invention the antigen is a polypeptide, e.g. a native polypeptide; a polypeptide produced by recombinant methods, including in vitro cell free synthesis, bacterial and prokaryotic expression systems; and the like.

Antigens may be exogenous (e.g., from a source other than the individual to whom the antigen is administered, e.g., from a different species) or endogenous (e.g., originating from within the host, e.g., a diseased element of body, a cancer antigen, a virus infected cell producing antigen, and the like). Antigens may be native (e.g., naturally-occurring); synthetic; or recombinant. Antigens include crude extracts; whole cells; and purified antigens, where "purified" indicates that the antigen is in a form that is enriched relative to the environment in which the antigen normally occurs and/or relative to the crude extract, for example, a cultured form of the antigen. The present disclosure is directed to compositions that optionally comprise an antigen or an antigenic peptide (e.g., epitope). Preferably, the antigen or antigenic peptide is recognized by autologous T cells. Any antigen may be used in the present invention that is displayed or detected on the surface of tumorous cells. In many cases, a patient will recognize such antigens a "non-self" or foreign. The antigen may be a wild type antigen or mutated relative to its wild type; or may be differentially post-translationally modified relative to the wild type.

It an embodiment of the invention, an antigen is a tumor-associated antigen. The antigen may be a neoantigen, and specifically a cancer neoantigen. Cancer neoantigens are tumor-specific antigens generated from gene mutations occurring in tumor cells. There are patient-specific somatic mutations occurring during neoplastic transformation that are particularly useful in the present invention.

Specific cancer antigens include, without limitation, for melanoma: Tyrosinase, Tyrosinase-related protein (Trp-1), gp100, Melan/MART-1; prostate adenocarcinoma; Prostate-specific membrane antigen, Prostate-specific acid phosphatase, Prostate-specific antigen; pancreatic, lung, breast and colon adenocarcinoma: MUC1; non-small-cell lung carcinoma: MUC1, MAGE antigens, EGFR; cancer/testis antigens: LAGE/NY-ESO1, MAGE antigens, CEA, AFP; breast cancer: HER-2; acute myelogenous leukemia: Aurora-A kinase, BRAP, Cyclin A1, hTert, WT1, chronic lymphocytic leukemia: ROR1; chronic myelogenous leukemia: BCR/ABL, BRAP, CML28, CML66, PR1, Proteinase 3, survivin, WT1.

Antigens recognized by T cells, whether helper T lymphocytes or CTL, are not recognized as intact proteins, but rather as small peptides that associate with class I or class II MHC proteins on the surface of cells. During the course of a naturally occurring immune response, antigens that are recognized in association with class I or II MHC molecules on antigen presenting cells (APCs) are acquired from outside the cell, internalized, and processed into small peptides that associate with the class I or II MHC molecules.

Antigens that give rise to proteins that are recognized in association with class I MHC molecules are generally proteins that are produced within the cells, and these antigens are processed and associate with class I MHC molecules. It is now understood that the peptides that associate with given class I or class II MHC molecules are characterized as having a common binding motif, and the binding motifs for a large number of different class I and II MHC molecules have been determined. Synthetic peptides can also be synthesized that correspond to the amino acid sequence of a given antigen and that contain a binding motif for a given class I or II MHC molecule. These peptides can then be added to appropriate APCs, and the APCs can be used to stimulate a T helper cell or CTL response either in vitro or in vivo. The binding motifs, methods for synthesizing the peptides, and methods for stimulating a T helper cell or CTL response are all known and readily available to one of ordinary skill in the art.

In an embodiment of the invention, the antigen is a peptide derived from MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, beta-Catenin, CDK4, Mum-1, p16, TAGE, PSMA, PSCA, CT7, telomerase, 43-9F, 5T4, 791Tgp72, alpha-fetoprotein, beta-HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, b-amyloid, CA125, CD40, EGFR, G17DT, GD2/3L, gp100, IMA950, KOC1, Peptidyl arginine deiminase-4, MUC-1, OFA, PANVAC, PAP, PSA, PSMA, SL701, SSX-2, TTK, TACAS, URLC10, vEGFR, WT-1.

In another embodiment, the antigen is present on the endogenous cancer cells of a patient suffering from cancer, such as melanoma, leukemia, ovarian, breast, colorectal, or lung squamous cancer, sarcoma, renal cell carcinoma, pancreatic carcinomas, squamous tumors of the head and neck, brain cancer, liver cancer, prostate cancer, ovarian cancer, and cervical cancer.

Compositions comprising an antigen protein or peptide are, or can be, made synthetically or by purification from a biological source. They can be made recombinantly. Desirably they are in some embodiments at least 90% pure, in some embodiments at least 92% pure, in some embodiments at least 93% pure, in some embodiments at least 94% pure, in some embodiments at least 95% pure, in some embodiments at least 96% pure, in some embodiments at least 97% pure, in some embodiments at least 98% pure, and in some embodiments at least 99% pure. For administration to a human, they generally do not contain other components that might be harmful to a human recipient.

Under certain circumstances it can be desirable to add additional antigenic proteins or antigenic peptides to the composition, for example, to make a cocktail having the ability to stimulate an immune response in a number of different HLA type hosts. Alternatively, additional proteins and/or peptides can provide an interacting function within a single host, such as but not limited to an adjuvant function or a stabilizing function. As a non-limiting example, tumor antigens can be used in admixture with the antigen peptides such that multiple different immune responses are induced in a single patient.

Conditions for Treatment

The terms “cancer,” “neoplasm,” and “tumor” are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase “cancer burden” refers to the quantum of cancer cells or cancer volume in a subject. Reducing cancer burden accordingly refers to reducing the number of cancer cells or the cancer volume in a subject. The term “cancer cell” as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias. Examples of cancer include but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

As is known in the art, cancer types can vary in the average or specific degree of mutation, where higher levels of mutation are associated with increased expression of neoantigens. See, for example, Vogelstein et al., (2013), supra. A low mutation burden can be a cancer type with an average per tumor, or specific number for an individual tumor, of up to about 10, up to about 20, up to about 30, up to about 40, up to about 50 non-synonymous mutations per tumor. A high mutation burden can be a cancer type with greater than about 50, greater than about 75, greater than about 100, greater than about 125, greater than about 150 non-synonymous mutations per tumor. A higher level of mutation may be associated with an improved response to a combination therapy of immunostimulatory nanoparticles with an immune checkpoint inhibitor.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable number of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

The types of cancer that can be treated using the subject methods of the present invention include but are not limited to adrenal cortical cancer, anal cancer, aplastic anemia, bile duct cancer, bladder cancer, bone cancer, bone metastasis, brain cancers, central nervous system (CNS) cancers, peripheral nervous system (PNS) cancers, breast cancer, cervical cancer, childhood Non-Hodgkin's lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's lymphoma, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcomas, melanoma skin cancer, non-melanoma skin cancers, stomach cancer, testicular cancer, thymus cancer, thyroid cancer, uterine cancer (e.g. uterine sarcoma), transitional cell carcinoma, vaginal cancer, vulvar cancer, mesothelioma, squamous cell or epidermoid carcinoma, bronchial adenoma, choriocarinoma, head and neck cancers, teratocarcinoma, or Waldenstrom's macroglobulinemia.

Dosage and frequency may vary depending on the half-life of the agent in the patient. It will be understood by one of skill in the art that such guidelines will be adjusted for the molecular weight of the active agent, the clearance from the blood, the mode of administration, and other pharmacokinetic parameters. The dosage may also be varied for localized administration, e.g. intranasal, inhalation, etc., or for systemic administration, e.g. i.m., i.p., i.v., oral, and the like.

Methods of Use

In the methods disclosed herein, an effective dose of an immunostimulatory composition as described herein is administered to a patient by administrations of immunostimulatory nanoparticles, in a manner effective to result in an improvement in the patient's condition. The timing of doses depends upon factors well known in the art. After the initial administration one or more booster doses may subsequently be administered to maintain antibody titers and efficacy of cell-mediated immunity. An example of a dosing regimen would be a dose on day 1, a second dose at from 1 to 2 months, a third dose at either 4, 6 or 12 months, and additional booster doses at distant times as needed. In one aspect, the invention provides a means for classifying the immune response to immunostimulatory, e.g., 9 to 15 weeks after administration of the immunostimulatory; by measuring the level of antibodies or responsive T cells against the cancer cells.

The formulation is administered by any suitable means, including intra-tumoral, transdermal, parenteral, subcutaneous, intraperitoneal, intrapulmonary, and intranasal. Parenteral infusions include intramuscular, intravenous, intraarterial, intraperitoneal, or subcutaneous administration. In addition, the formulation may be suitably administered by pulse infusion, particularly with declining doses.

In another embodiment of the invention, an article of manufacture containing materials useful for the methods described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is one or more antibodies in a formulation of the invention as described above. The label on, or associated with, the container indicates that the composition is used for treating the condition of choice. The article of manufacture may further comprise a second container comprising a pharmaceutically acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

Therapeutic formulations are prepared for storage by mixing the nanoparticles having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The composition will be formulated, dosed, and administered in a fashion consistent with good medical practice. The "therapeutically effective amount" of the formulation to be administered will be governed by clinical considerations.

The therapeutic dose of adjuvant may be at least about 0.01 μg/kg body weight, at least about 0.05 μg/kg body weight; at least about 0.1 μg/kg body weight, at least about 0.5 μg/kg body weight, at least about 1 μg/kg body weight, at least about 2.5 μg/kg body weight, at least about 5 μg/kg body weight, and not more than about 100 μg/kg body weight. It will be understood by one of skill in the art that such guidelines will be adjusted for the molecular weight of the active agent, and as required. The dosage may also be varied for localized administration, or for systemic administration, e.g. i.m., i.p., i.v., and the like.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

Combination Therapies

The immunostimulatory nanoparticles may be administered in a combination therapy with an effective dose or doses of a second immune regulatory agent, e.g. immune checkpoint inhibitors that reverse the inhibition of immune responses through administering antagonists of inhibitory signals, agonists of immune costimulatory molecules to increase responsiveness. In some embodiments a synergistic response is observed, relative to the level of anti-tumor activity observed with either agent administered singly, or may include, for example, targeted therapeutics, antibodies specific for tumor antigens, and the like. The dose of immune checkpoint inhibitor, for example, may be equal to, or less than the effective dose administered in the absence of the immunostimulatory nanoparticles.

Immune-checkpoint receptors that have been most actively studied in the context of clinical cancer immunotherapy, cytotoxic T-lymphocyte-associated antigen 4 (CTLA4; also known as CD152) and programmed cell death protein 1 (PD1; also known as CD279)—are both inhibitory receptors. The clinical activity of antibodies that block either of these receptors implies that antitumor immunity can be enhanced at multiple levels and combinatorial strategies can be intelligently designed, guided by mechanistic considerations and preclinical models.

CTLA4 is expressed exclusively on T cells where it primarily regulates the amplitude of the early stages of T cell activation. CTLA4 counteracts the activity of the T cell co-stimulatory receptor, CD28. CD28 and CTLA4 share identical ligands: CD80 (also known as B7.1) and CD86 (also known as B7.2). The major physiological roles of CTLA4 are downmodulation of helper T cell activity and enhancement of regulatory T (TReg) cell immunosuppressive activity. CTLA4 blockade results in a broad enhancement of immune responses. Two fully humanized CTLA4 antibodies, ipilimumab and tremelimumab, are in clinical testing and use. Clinically the response to immune-checkpoint blockers is slow and, in many patients, delayed up to 6 months after treatment initiation. In some cases, metastatic lesions actually increase in size on computed tomography (CT) or magnetic resonance imaging (MRI) scans before regressing. Anti-CTLA4 antibodies that antagonize this inhibitory immune function are very potent therapeutics but have significant side effects since this enables T cell activity against the self that is usually inhibited through these inhibitory molecules and pathways.

In some embodiments the dose of anti-CTLA4 agent administered in a combination therapy is reduced to a level that minimizes undesirable side effects, e.g. at a dose that is up to about 90% of the currently approved dose, that is up to about 80%, up to about 70%, up to about 60%, up to about 50%, up to about 40%, up to about 30%, up to about 20%, up to about 10%, up to about 5% of a conventional dose. In some embodiments the number of doses is reduced, e.g. dosing with anti-CTLA4 agent not more than 1×, not more than 2×, not more than 3×, etc. As a reference, for example, current protocols usually call for administration of ipilimumab at a dose of 3 mg/kg, administered every 3 weeks for a total of 4 doses; optionally in combination with additional agents such as, for example dacarbazine or temozolomide; or with peptide vaccines. Other protocols have explored administration of ipilimumab at the dose of 10 mg/kg as a single agent against metastatic melanoma.

Tremelimumab has been administered as a single antibody infusion at doses ranging from 0.01 mg/kg to 15 mg/kg. Objective responses were evident at doses of 3 mg/kg and above. The majority of responses were noted in patients that achieved sustained plasma levels of tremelimumab beyond 30 μg/ml at one month. The doses of 10 mg/kg administered every month and 15 mg/kg administered every 3 months have been studied further in a phase II randomized clinical trial, however toxicity was doubled when dosing more frequently with the 10 mg/kg monthly regimen. Based on these data, single agent tremelimumab at 15 mg/kg every 3 months was chosen for clinical trials.

For some patients, the ability of CTLA-4 blockade to activate the immune system results in inflammatory manifestations characterized as immune-related adverse events (irAEs). The most clinically significant irAE is enterocolitis which can range in severity; grade III/IV enterocolitis is seen in ~15% of patients treated with ipilimumab at 10 mg/kg. Additional irAEs include rash/pruritus (>50%), hepatitis (5-10%), hypophysitis (5%), uveitis (<2%), pancreatitis (<2%), and leucopenia (<2%). The combination of agents may reduce such adverse events. In some embodiments of the invention a method is provided for treating cancer with a combination of an agents, where the dosing of agents in the combination provides for a treatment of cancer with a clinically significant reduction in immune-related adverse events relative to the dosing required for anti-CTLA-4 in the absence of the immunostimulatory particles.

Other immune-checkpoint proteins are PD1 and PDL1. Three anti-PD-1 antibodies have been approved by the FDA: pembrolizumab (Keytruda), nivolumab (Opdivo), and cemiplimab (Libtayo). Anti-PD1 agents in clinical trials include, for example, JTX-4014; Spartalizumab (PDR001); Camrelizumab (SHR1210); Sintilimab (IB1308); Tislelizumab (BGB-A317) is a humanized IgG4 anti-PD-1 monoclonal antibody; Toripalimab (JS 001) is a humanized IgG4 monoclonal antibody against PD-1; INCMGA00012 (MGA012) is a humanized IgG4 monoclonal antibody; AMP-224; AMP-514 (MED10680).

The major role of PD1 is to limit the activity of T cells in peripheral tissues at the time of an inflammatory response to infection and to limit autoimmunity. PD1 expression is induced when T cells become activated. When engaged by one of its ligands, PD1 inhibits kinases that are involved in T cell activation. PD1 is highly expressed on $T_{Reg}$ cells, where it may enhance their proliferation in the presence of ligand. Because many tumors are highly infiltrated with $T_{Reg}$ cells, blockade of the PD1 pathway may also enhance antitumor immune responses by diminishing the number and/or suppressive activity of intratumoral $T_{Reg}$ cells.

The two ligands for PD1 are PD1 ligand 1 (PDL1; also known as B7-H1 and CD274) and PDL2 (also known as B7-DC and CD273). Approved for clinical use are Atezolizumab (Tecentriq) is a fully humanised IgG1 (immunoglobulin 1) antibody; Avelumab (Bavencio) is a fully human IgG1 antibody; Durvalumab (Imfinzi) is a fully human IgG1 antibody. PD-L1 inhibitors in clinical trials include KN035 with subcutaneous formulation; CK-301; AUNP12; CA-170; BMS-986189.

PD1 ligands are commonly upregulated on the tumor cell surface from many different human tumors. On cells from solid tumors, the major PD1 ligand that is expressed is PDL1. PDL1 is expressed on cancer cells and through binding to its receptor PD1 on T cells it inhibits T cell activation/function. Therefore, PD1 and PDL1 blocking agents can overcome this inhibitory signaling and maintain or restore anti-tumor T cell function. However, since PDL1 is expressed on tumor cells, antibodies that bind and block PDL1 can also enable ADCP, ADCC, and CDC of tumor cells. Thus a combination of anti-PDL1 agents with immunostimulatory agents can enhance the anti-tumor potency. These agents may be administered together (over the same course of treatment, not necessarily the same day and frequency).

Lymphocyte activation gene 3 (LAG3; also known as CD223), 2B4 (also known as CD244), B and T lymphocyte attenuator (BTLA; also known as CD272), T cell membrane protein 3 (TIM3; also known as HAVcr2), adenosine A2a receptor (A2aR) and the family of killer inhibitory receptors have each been associated with the inhibition of lymphocyte activity and in some cases the induction of lymphocyte anergy. Antibody targeting of these receptors can be used in the methods of the invention.

LAG3 is a CD4 homolog that enhances the function of $T_{Reg}$ cells. LAG3 also inhibits $CD8^+$ effector T cell functions independently of its role on $T_{Reg}$ cells. The only known ligand for LAG3 is MHC class II molecules, which are expressed on tumor-infiltrating macrophages and dendritic cells. LAG3 is one of various immune-checkpoint receptors that are coordinately upregulated on both $T_{Reg}$ cells and anergic T cells, and simultaneous blockade of these receptors can result in enhanced reversal of this anergic state relative to blockade of one receptor alone. In particular, PD1 and LAG3 are commonly co-expressed on anergic or exhausted T cells. Dual blockade of LAG3 and PD1 synergistically reversed anergy among tumor-specific $CD8^+$ T cells and virus-specific $CD8^+$ T cells in the setting of chronic infection. LAG3 blocking agents can overcome this inhibitory signaling and maintain or restore anti-tumor T cell function.

TIM3 inhibits T helper 1 ($T_H1$) cell responses, and TIM3 antibodies enhance antitumor immunity. TIM3 has also been reported to be co-expressed with PD1 on tumor-specific $CD8^+$ T cells. Tim3 blocking agents can overcome this inhibitory signaling and maintain or restore anti-tumor T cell function.

BTLA is an inhibitory receptor on T cells that interacts with TNFRSF14. $BTLA^{hi}$ T cells are inhibited in the presence of its ligand. The system of interacting molecules is complex: CD160 (an immunoglobulin superfamily member) and LIGHT (also known as TNFSF14), mediate inhibitory and co-stimulatory activity, respectively. Signaling can be bidirectional, depending on the specific combination of interactions. Dual blockade of BTLA and PD1 enhances antitumor immunity.

A2aR, the ligand of which is adenosine, inhibits T cell responses, in part by driving $CD4^+$ T cells to express FOXP3 and hence to develop into $T_{Reg}$ cells. Deletion of this receptor results in enhanced and sometimes pathological inflammatory responses to infection. A2aR can be inhibited either by antibodies that block adenosine binding or by adenosine analogues.

Agents that agonize an immune costimulatory molecule are also useful in the methods of the invention. Such agents include agonists or CD40 and OX40. CD40 is a costimulatory protein found on antigen presenting cells (APCs) and is required for their activation. These APCs include phagocytes (macrophages and dendritic cells) and B cells. CD40 is part of the TNF receptor family. The primary activating signaling molecules for CD40 are IFNγ and CD40 ligand (CD40L). Stimulation through CD40 activates macrophages. Agonistic CD40 agents may be administered substantially simultaneously with immunostimulatory agents; or may be administered prior to and concurrently with treatment.

OX40 (CD134) is a member of the TNFR super-family and expressed on T cells. Molecules that bind OX40 can stimulate proliferation and differentiation of T cells.

Other immuno-oncology agents that can be administered in combination according to the methods described herein include antibodies specific for chemokine receptors, including without limitation anti-CCR4 and anti-CCR2. Anti CCR4 (CD194) antibodies of interest include humanized monoclonal antibodies directed against C-C chemokine receptor 4 (CCR4) with potential anti-inflammatory and antineoplastic activities. Exemplary is mogamulizumab, which selectively binds to and blocks the activity of CCR4, which may inhibit CCR4-mediated signal transduction pathways and, so, chemokine-mediated cellular migration and proliferation of T cells, and chemokine-mediated angiogenesis. In addition, this agent may induce antibody-dependent cell-mediated cytotoxicity (ADCC) against CCR4-positive T cells. CCR4, a G-coupled-protein receptor for C-C chemokines such MIP-1, RANTES, TARC and MCP-1, is expressed on the surfaces of some types of T cells, endothelial cells, and some types of neurons. CCR4, also known as CD194, may be overexpressed on adult T-cell lymphoma (ATL) and peripheral T-cell lymphoma (PTCL) cells.

Anti-CCR2 (CD192) Ab. CCR2 is expressed on inflammatory macrophages that can be found in various inflammatory conditions, e.g. rheumatoid arthritis; and have also been identified as expressed on tumor promoting macrophages. Chemokines that bind to CCR2, e.g. CCL2, can recruit and activate the inflammatory macrophages. Inhibiting the chemokine signaling through CCR2 with anti-CCR2 antibodies may result in lower frequencies of undesirable autoimmune or tumor promoting macrophages through inhibition of recruiting or antibody dependent depletion, resulting in mitigation of autoimmune diseases like rheumatoid arthritis, or inhibition of tumor growth or metastasis. CCR2 is also expressed on regulatory T cells, and the CCR2 ligand, CCL2, mediates recruitment of regulatory T cells into tumors. Regulatory T cells suppress a response for anti-tumor T cells and thus their inhibition or depletion is desired. Anti-CCR2 Ab is administered in combination for enhanced depletion of CCR2 positive inflammatory and tumor promoting macrophages and regulatory T cells. Inflammatory (tumor associated macrophages) and regulatory T cells suppress an anti-tumor immune response and therefore their inhibition or depletion is desired.

Therapeutic combinations with immunostimulatory compositions of the disclosure may include treatment with anti-CD47 agents, e.g. Magrolimab, Abitrexate (Methotrexate Injection), Abraxane (Paclitaxel Injection), Adcetris (Brentuximab Vedotin Injection), Adriamycin (Doxorubicin), Adrucil Injection (5-FU (fluorouracil)), Afinitor (Everolimus), Afinitor Disperz (Everolimus), Alimta (PEMET EXED), Alkeran Injection (Melphalan Injection), Alkeran Tablets (Melphalan), Aredia (Pamidronate), Arimidex (Anastrozole), Aromasin (Exemestane), Arranon (Nelarabine), Arzerra (Ofatumumab Injection), Avastin (Bevacizumab), Bexxar (Tositumomab), BiCNU (Carmustine), Blenoxane (Bleomycin), Bosulif (Bosutinib), Busulfex Injection (Busulfan Injection), Campath (Alemtuzumab), Camptosar (Irinotecan), Caprelsa (Vandetanib), Casodex (Bicalutamide), CeeNU (Lomustine), CeeNU Dose Pack (Lomustine), Cerubidine (Daunorubicin), Clolar (Clofarabine Injection), Cometriq (Cabozantinib), Cosmegen (Dactinomycin), CytosarU (Cytarabine), Cytoxan (Cytoxan), Cytoxan Injection (Cyclophosphamide Injection), Dacogen (Decitabine), DaunoXome (Daunorubicin Lipid Complex Injection), Decadron (Dexamethasone), DepoCyt (Cytarabine Lipid Complex Injection), Dexamethasone Intensol (Dexamethasone), Dexpak Taperpak (Dexamethasone), Docefrez (Docetaxel), Doxil (Doxorubicin Lipid Complex Injection), Droxia (Hydroxyurea), DTIC (Decarbazine), Eligard (Leuprolide), Ellence (Ellence (epirubicin)), Eloxatin (Eloxatin (oxaliplatin)), Elspar (Asparaginase), Emcyt (Estramustine), Erbitux (Cetuximab), Erivedge (Vismodegib), Erwinaze (Asparaginase *Erwinia chrysanthemi*), Ethyol (Amifostine), Etopophos (Etoposide Injection), Eulexin (Flutamide), Fareston (Toremifene), Faslodex (Fulvestrant), Femara (Letrozole), Firmagon (Degarelix Injection), Fludara (Fludarabine), Folex (Methotrexate Injection), Folotyn (Pralatrexate Injection), FUDR (FUDR (floxuridine)), Gemzar (Gemcitabine), Gilotrif (Afatinib), Gleevec (Imatinib Mesylate), Gliadel Wafer (Carmustine wafer), Halaven (Eribulin Injection), Herceptin (Trastuzumab), Hexalen (Altretamine), Hycamtin (Topotecan), Hycamtin (Topotecan), Hydrea (Hydroxyurea), Iclusig (Ponatinib), Idamycin PFS (Idarubicin), Ifex (Ifosfamide), Inlyta (Axitinib), Intron A alfab (Interferon alfa-2a), Iressa (Gefitinib), Istodax (Romidepsin Injection), Ixempra (Ixabepilone Injection), Jakafi (Ruxolitinib), Jevtana (Cabazitaxel Injection), Kadcyla (Ado-trastuzumab Emtansine), Kyprolis (Carfilzomib), Leukeran (Chlorambucil), Leukine (Sargramostim), Leustatin (Cladribine), Lupron (Leuprolide), Lupron Depot (Leuprolide), Lupron DepotPED (Leuprolide), Lysodren (Mitotane), Marqibo Kit (Vincristine Lipid Complex Injection), Matulane (Procarbazine), Megace (Megestrol), Mekinist (Trametinib), Mesnex (Mesna), Mesnex (Mesna Injection), Metastron (Strontium-89 Chloride), Mexate (Methotrexate Injection), Mustargen (Mechlorethamine), Mutamycin (Mitomycin), Myleran (Busulfan), Mylotarg (Gemtuzumab Ozogamicin), Navelbine (Vinorelbine), Neosar Injection (Cyclophosphamide Injection), Neulasta (filgrastim), Neulasta (pegfilgrastim), Neupogen (filgrastim), Nexavar (Sorafenib), Nilandron (Nilandron (nilutamide)), Nipent (Pentostatin), Nolvadex (Tamoxifen), Novantrone (Mitoxantrone), Oncaspar (Pegaspargase), Oncovin (Vincristine), Ontak (Denileukin Diftitox), Onxol (Paclitaxel Injection), Panretin (Alitretinoin), Paraplatin (Carboplatin), Perjeta (Pertuzumab Injection), Platinol (Cisplatin), Platinol (Cisplatin Injection), PlatinolAQ (Cisplatin), PlatinolAQ (Cisplatin Injection), Pomalyst (Pomalidomide), Prednisone Intensol (Prednisone), Proleukin (Aldesleukin), Purinethol (Mercaptopurine), Reclast (Zoledronic acid), Revlimid (Lenalidomide), Rheumatrex (Methotrexate), Rituxan (Rituximab), RoferonA alfaa (Interferon alfa-2a), Rubex (Doxorubicin), Sandostatin (Octreotide), Sandostatin LAR Depot (Octreotide), Soltamox (Tamoxifen), Sprycel (Dasatinib), Sterapred (Prednisone), Sterapred DS (Prednisone), Stivarga (Regorafenib), Supprelin LA (Histrelin Implant), Sutent (Sunitinib), Sylatron (Peginterferon Alfa-2b Injection (Sylatron)), Synribo (Omacetaxine Injection), Tabloid (Thioguanine), Taflinar (Dabrafenib), Tarceva (Erlotinib), Targretin Capsules (Bexarotene), Tasigna (Decarbazine), Taxol (Paclitaxel Injection), Taxotere (Docetaxel), Temodar (Temozolomide), Temodar (Temozolomide Injection), Tepadina (Thiotepa), Thalomid (Thalidomide), TheraCys BCG (BCG), Thioplex (Thiotepa), TICE BCG (BCG), Toposar (Etoposide Injection), Torisel (Temsirolimus), Treanda (Bendamustine hydrochloride), Trelstar (Triptorelin Injection), Trexall (Methotrexate), Trisenox (Arsenic trioxide), Tykerb (lapatinib), Valstar (Valrubicin Intravesical), Vantas (Histrelin Implant), Vectibix (Panitumumab), Velban (Vinblastine), Velcade (Bortezomib), Vepesid (Etoposide), Vepesid (Etoposide Injection), Vesanoid (Tretinoin), Vidaza (Azacitidine), Vincasar PFS (Vincristine), Vincrex (Vincristine), Votrient (Pazopanib), Vumon (Teniposide), Wellcovorin IV (Leucovorin Injection), Xalkori (Crizotinib), Xeloda (Capecitabine), Xtandi (Enzalutamide), Yervoy (Ipilimumab Injection), Zaltrap (Ziv-aflibercept Injection), Zanosar (Streptozocin), Zelboraf (Vemurafenib), Zevalin (Ibritumomab Tiuxetan), Zoladex (Goserelin), Zolinza (Vorinostat), Zometa (Zoledronic acid), Zortress (Everolimus), Zytiga (Abiraterone), Nimotuzumab and immune checkpoint inhibitors such as nivolumab, pembrolizumab/MK-3475, pidilizumab and AMP-224 targeting PD-1; and BMS-935559, MED14736, MPDL3280A and MSB0010718C targeting PD-L1 and those targeting CTLA-4 such as ipilimumab.

Radiotherapy means the use of radiation, usually X-rays, to treat illness. X-rays were discovered in 1895 and since then radiation has been used in medicine for diagnosis and investigation (X-rays) and treatment (radiotherapy). Radiotherapy may be from outside the body as external radiotherapy, using X-rays, cobalt irradiation, electrons, and more rarely other particles such as protons. It may also be from within the body as internal radiotherapy, which uses radioactive metals or liquids (isotopes) to treat cancer.

The invention now being fully described, it will be apparent to one of ordinary skill in the art that various changes and modifications can be made without departing from the spirit or scope of the invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all of the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 1

Toll-Like Receptor Agonist Containing Nanoparticles for Cancer Immunotherapy in Multiple Cancer Models By uniquely utilizing gardiquimod, a TLR7 agonist sharing a similar imidazoquinoline structure with imiquimod, as a drug initiator for the ring-opening polymerization of lactide (LA) and nanoparticle (NP) formulation, we successfully demonstrated the development of highly biocompatible TLR7 agonist-based nanoparticles (TLR7-NPs) for bolstering the body's anti-cancer immune responses, and reducing systemic toxicities (acute vascular leak syndrome) often associated with pulsatile global immunostimulation.

The methods disclosed herein produce TLR7-NPs with well-controlled physicochemical properties, including sub-100 nm size, very narrow size distributions, predefined drug loading, precisely defined composition, and tunable drug release kinetics. With these optimal physicochemical properties, this NP system can mobilize and activate dendritic cells and cells of the monocytic lineage in tumor draining lymph nodes (dLNs), leading to subsequent robust induction of T cell responses.

Importantly, in situ injection with TLR7-NPs+/−anti-PD-1 was effective against tumors of a variety of histologic types, such as colon cancer (MC38), pancreatic cancer (Pan02) and glioblastoma (GL261). Strikingly, systemic administration of TLR7-NPs alone also efficiently delays tumor growth and induces 37.5% of complete responses in orthotropic glioblastoma-bearing mice.

Results and Discussion

Synthesis and characterization of gardiquimod-polylactide nanoparticles (TLR7-NPs). The TLR7-NPs were constructed through co-nanoprecipitation of TLR7-PLA polymer conjugates and poly(ethylene glycol)-b-poly(lactic-co-glycolic acid) (PEG-PLGA) (FIG. 1*a*). TLR7-PLA polymer conjugates were synthesized by using gardiquimod, a potent agonist for TLR7 receptor expressed in both mouse and human, to initiate the ring-opening polymerization (ROP) of lactide. In detail, gardiquimod (3.1 mg, 0.01 mmol) was dissolved in anhydrous THE (300 μL) and mixed with a THE solution (500 μL) containing (BDI-EI)ZnN-$(TMS)_2$ [(BDI) is 2-((2,6-diethylphenyl) amido)-4-((2,6-diisopropylphenyl)-imino)-2-pentene] (6.5 mg, 0.01 mmol). The mixture was stirred for 15 min. LA (36 mg, 25 eq) was dissolved in THE (500 μL) and added to the stirred mixture. The polymerization proceeded in the glovebox overnight. After LA was completely consumed, the reaction was stopped by quenching the polymerization solution with cold methanol solution (30 μL). The polymer was precipitated with ether (10 mL), collected by centrifugation, and dried by vacuum. This method allowed for quantitative incorporation of gardiquimod into PLA polymers and resulted in TLR7-PLA conjugates with precisely controlled composition and molecular weights. At a monomer/initiator (LA/gardiquimod) ratio of 25, gardiquimod loading was achieved as high as 14.8 wt % with nearly 100% incorporation efficiency. The resultant TLR7-PLA polymer conjugates were then dissolved in dimethylformamide (DMF) at concentration of 10 mg/mL and mixed with PEG-PLGA (DMF, 10 mg/mL) (1/1, v/v) and added dropwisely into rapidly stirred water to self-assemble into TLR7-NPs with 77 nm hydrodynamic diameter and narrow size distributions (polydispersity index=0.105) characterized by dynamic light scattering (DLS) (FIG. 1*b*).

In the design of TLR7-NPs, gardiquimod was conjugated to PLA polymer through ester linkages and could be released from NPs subjected to hydrolysis of ester bonds in the physiological condition. Released gardiquimod from TLR7-NPs (red) shared the identical UV-vis absorbance spectrum as the original gardiquimod compound (black) providing evidence of releasing unmodified TLR7 agonist without any residual chemical groups (FIG. 1*c*). To mimic the release profile of gardiquimod from TLR7-NPs in the body, we next conduct the kinetic studies of TLR7-NPs at different pH 5.0 and 7.4. Consistent with expectations, gardiquimod was release from NPs in a sustained manner without burst release effects, potentially minimizing the undesired systemic toxicities during the circulation; the release rate of gardiquimod from NPs was accelerated at increased acidities, likely due to faster hydrolysis at lower pH, which is important for robust activation of the intracellular TLR7 receptors once NPs are internalized into cells (FIG. 1*d*).

Figure 2B:
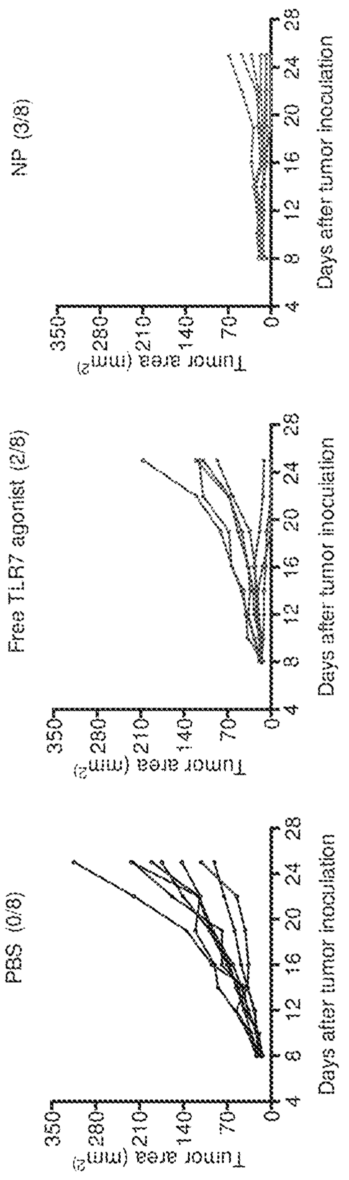
Figure 2C:
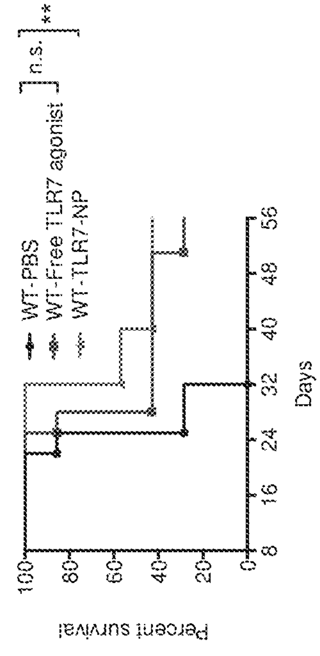
Figure 2D:
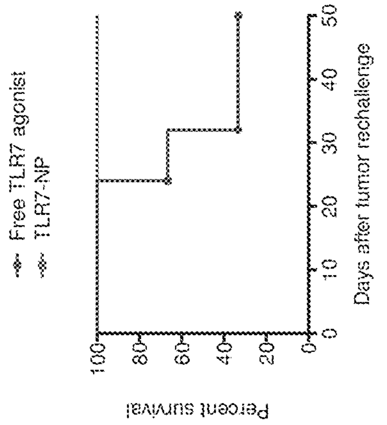

Therapeutic efficacy of TLR7-NPs in the subcutaneous MC38 colon carcinoma. We first evaluated the therapeutic efficacy of TLR7-NPs in murine MC38 colon carcinoma. C57BL/6 mice were inoculated with 0.5 million MC38 tumor cells at subcutaneous flank and intratumorally treated on day 8, day 11 and day 14 with TLR7 agonist in either soluble (free-TLR7) or nanoparticle forms (TLR7-NPs) (equivalent dose of gardiquimod: 20 μg). Results revealed a robust therapeutic effect of NPs in this tumor model with a strong inhibition of tumor growth (FIGS. 2A and 2B) and prolonged overall survival (FIG. 2C). Strikingly, TLR7-NPs treatment-induced durable cures in 37.5% of the mice (FIG. 2B), and all of these rejected a second tumor challenge at Day 70, indicating the establishment of effective immunological memory (FIG. 2D). On the other hand, free-TLR7 treatment had only 25% of mice with complete responses (FIG. 2B). Interestingly, only 33% of these mice survivors were able to reject a second tumor challenge (FIG. 2D).

Figure 3A:
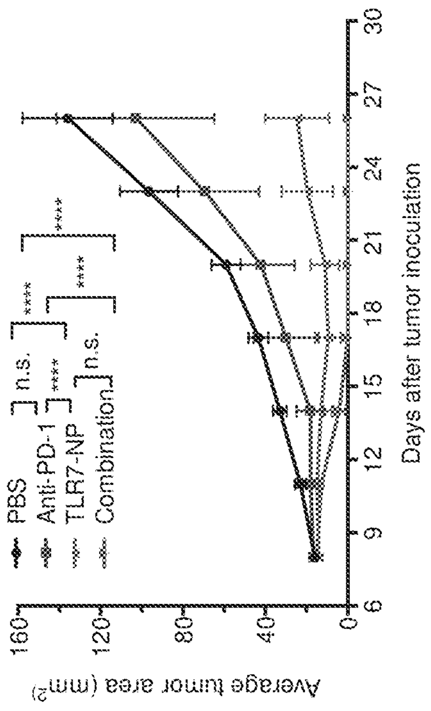
FIG. 3A-3C. Tumor eradiation by combination immunotherapy with TLR7-NPs and anti-PD-1 checkpoint blockade. C57BL/6 mice were inoculated subcutaneously with $5\times10^5$ MC38 tumor cells and treated with PBS, TLR7-NPs, anti-PD-1, and combination of TLR7-NPs and anti-PD-1, respectively on days 11, 14, 17, 20. Average and individual MC38 tumor growth curves are shown in (a) and (b). n.s. no statistical significance; * $p<0.001$; ** $p<0.0001$ analyzed by two-way ANOVA. (c) The percentage survival of mice bearing MC38 tumors after four treatments was monitored over time. n.s. no statistical significance; * $p<0.05$;  $p<0.01$; * $p<0.001$. Data was analyzed by Log-rank (Mantel-Cox) test.
Figure 3C:
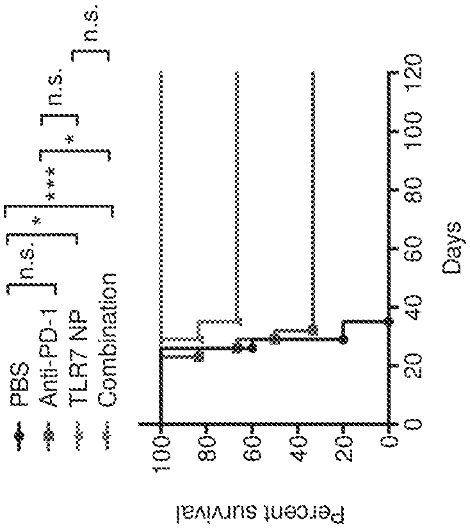
Figure 3B:
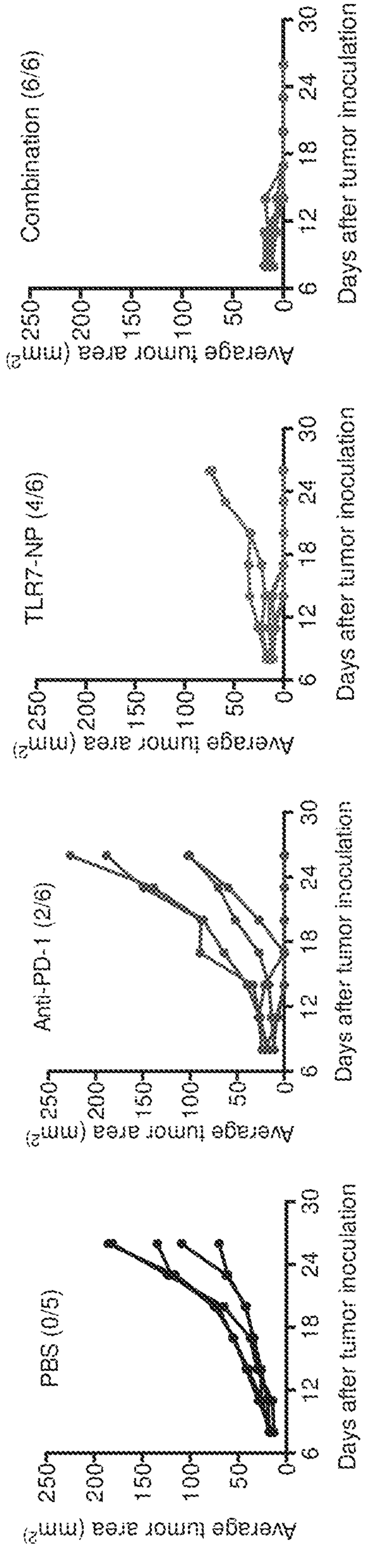

Synergistic effect between TLR7-NPs and anti-PD-1 in subcutaneous mouse MC38 colon carcinoma. We next examined the therapeutic efficacy of TLR7-NPs treatment combined with anti-PD-1 therapy. C57BL/6 mice bearing MC38 colon cancers at subcutaneous flank were treated four times with PBS, anti-PD-1 alone, TLR7-NPs alone, or anti-PD-1 plus TLR7-NPs every three days starting at Day 8. Results showed anti-PD-1 therapy only elicited partial response with only 2 out of 6 mice rejected tumors (FIGS. 3A and 3B). TLR7-NPs alone efficiently slowed tumor growth (FIG. 3A) and eliminated tumors in 4 of 6 animals (FIG. 3B). Strikingly, the combination therapy of anti-PD-1 and TLR7-NPs led to remarkable antitumor efficacy and elimination of established tumors in 100% of animals (FIGS. 3B and 3C). When rechallenged with MC38 tumor cells at day 120, all surviving animals from the TLR7-NPs plus anti-PD-1 group were protected against tumor growth, indicating long-term antitumor memory response. Taken together, these results demonstrated that TLR7-NPs combined with immune checkpoint blockade therapy anti-PD-1 exerted robust antitumor efficacy against subcutaneous MC38 tumors.

Figure 4:
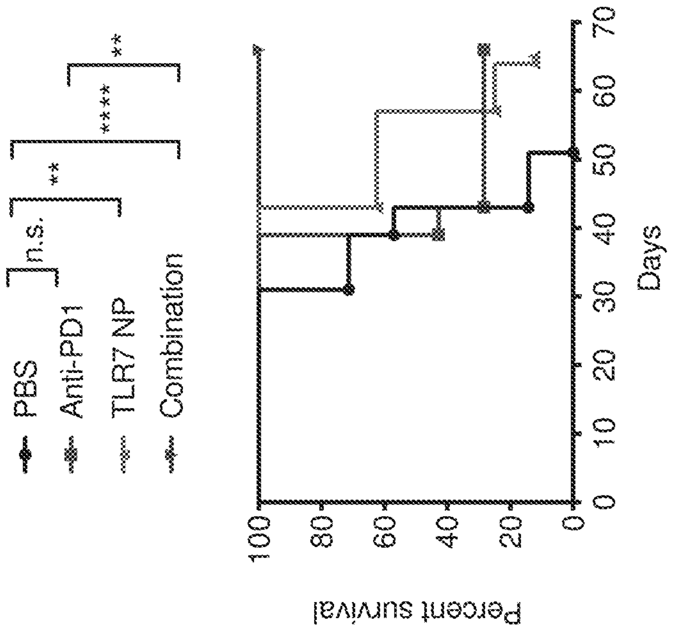
FIG. 4. Combination immunotherapy of TLR7-NPs and anti-PD-1 checkpoint blockade effectively prolongs overall survival of mice in pancreatic ductal adenocarcinoma (PDAC) model. C57BL/6 mice were inoculated subcutaneously with $1\times10^6$ Pan02 tumor cells and treated with PBS, TLR7-NPs, anti-PD-1, and combination of TLR7-NPs and anti-PD-1, respectively on days 6, 9, 12, and 15. The percentage survival of mice bearing pan02 PDAC tumors after four treatments was monitored over time. n.s. no statistical significance;  $p<0.01$; ** $p<0.0001$. Data was analyzed by Log-rank (Mantel-Cox) test.

Synergistic effect between TLR7-NPs and anti-PD-1 in subcutaneous mouse pancreatic ductal adenocarcinoma. We next examined the therapeutic efficacy of TLR7-NPs combined with anti-PD-1 therapy in mouse pancreatic ductal adenocarcinoma (PDAC) model. C57BL/6 mice were inoculated with 1 million Pan02 pancreatic cancer cells at subcutaneous flank. When the tumors were fully established at day 6, mice were separated into 4 groups with similar tumors sizes and received the treatments of PBS, anti-PD-1 alone, TLR7-NPs alone, or anti-PD-1 plus TLR7-NPs every three days for 4 times. Results showed anti-PD-1 alone had minimal impact on mouse survival without any statistical significance compared to PBS control. In contrast, TLR7-NPs alone significantly prolong mouse survival compared to anti-PD-1 treatment alone (FIG. 4). Remarkably, the combination of TLR7-NPs and anti-PD-1 resulted in complete regression of all the mouse bearing Pan02 PDAC. Most importantly, tumor regressions in response to the combined treatment were long-lasting (FIG. 4).

Figures 5A, 5B, 5C:
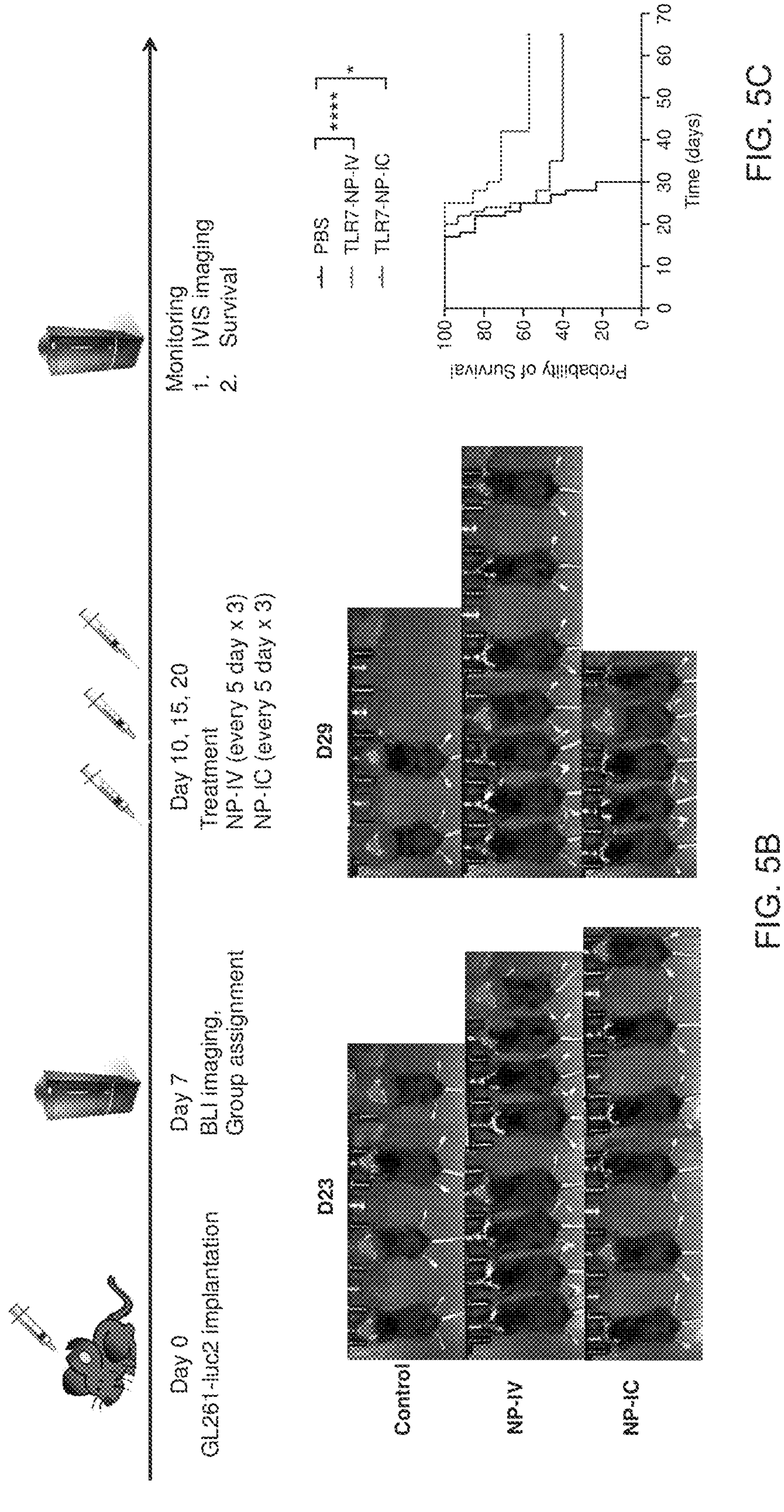
FIG. 5A-5C. Anti-tumor efficacy exerted by TLR7-NPs via both intracranial (IC) and intravenous (IV) injections in orthotopic GL261 glioblastoma model. (a) Treatment regimen and study timeline. (b) Luminescent imaging of tumor burden following therapy of TLR7-NPs via both IC and IV injections on day 23 and day 29. (c) The percentage survival of mice bearing GL261 glioblastoma after three treatments was monitored over time *$p<0.05$. **** $p<0.0001$ Data was combined from two individual experiments and analyzed by Log-rank (Mantel-Cox) test.
Figure 6A:
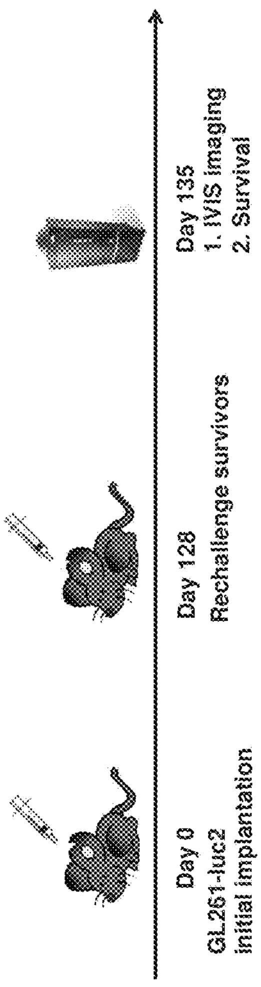
FIG. 6A-6C. Both intracranial and intravenous injection of TLR7-NPs establishes the effective immune memory against GL261. (a) Study timeline. (b) Luminescent imaging of tumor burden of control mice, survivors from both intracranial TLR7-NPs treatment and intravenous TLR7-NPs treatment on day 135 (7 days post tumor rechallenge). (c) The percentage survival of mice survivors after tumor rechallenges on day 128.
Figure 6B:
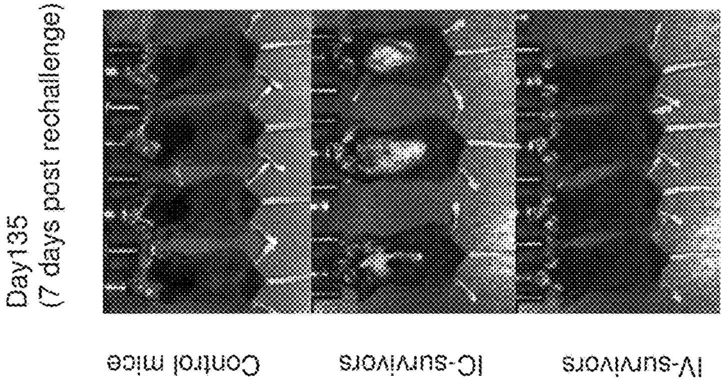
Figure 6C:
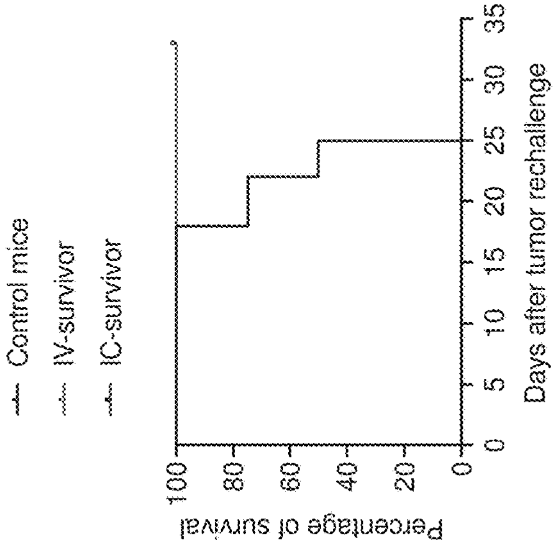

Therapeutic efficacy of TLR7-NPs in an orthotopic GL261 glioma model. Having shown immunogenicity and potency of TLR7-NPs+/−anti-PD-1 in the subcutaneous flank model, we proceeded to assess the therapeutic efficacy of TLR7-NPs in an orthotopic glioblastoma model (GL261-Luc2), in which in vivo tumor burden was demonstrated to be well correlated with bioluminescent signal intensity. C57BL/6 mice were inoculated with 130,000 GL261-Luc2 cells via stereotactic injection into the right striatum on day 0. Seven days following tumor inoculation, mice were imaged and equally distributed based upon bioluminescent intensities into three groups: PBS, TLR7-NP intracranial (IC) injection, and TLR7-NP intravenous (IV) injection. Following randomization, mice received IC or IV therapy every five days for three times and were monitored non-invasively by bioluminescence imaging technique (FIG. 5A). As shown in bioluminescence images on day 23 and 29 (FIG. 5B), both TLR7-NP-IC and TLR7-NP-IV significantly slowed primary tumor growth compared to PBS-treated mice. Notably, 5 out of 14 (35.71%) mice treated with TLR7-NP-IC and 7 out of 14 (50.0%) treated with TLR7-NP-IV showed complete tumor responses. In addition, both TLR7-NP-IC and TLR7-NP-IV groups remarkably prolonged the overall survival of tumor-bearing mice (FIG. 5C). When rechallenged with GL261 tumor cells at day 135, all surviving animals from TLR7-NPs-IC and TLR7-NP-IV groups were protected against tumor growth, indicating long-term antitumor memory response (FIG. 6). Overall, both TLR7-NP-IC and TLR7-NP-IV therapy exerted strong antitumor efficacy in a murine model of orthotopic glioblastoma.

The combination of TLR7-NPs and anti-PD-1 significantly boosted the response rate to anti-PD-1 in an orthotopic GL261 glioma model. We also examined the therapeutic efficacy of TLR7-NPs combined with anti-PD-1 therapy in the orthotopic GL261-Luc2 glioblastoma model. Seven days following tumor inoculation, mice were imaged and equally distributed based upon bioluminescent intensities into three groups: PBS, anti-PD-1 injection, and anti-PD-1 plus TLR7-NP-IV treatment. As shown in bioluminescence images 7 days post-treatment, TLR7-NPs-IV showed a synergistic effect with anti-PD-1, leading to 67% (4 out of 6) mice rejecting tumors, while anti-PD-1 alone only showed tumor eradication in 20% of mice (FIG. 7B).

Figure 8A:
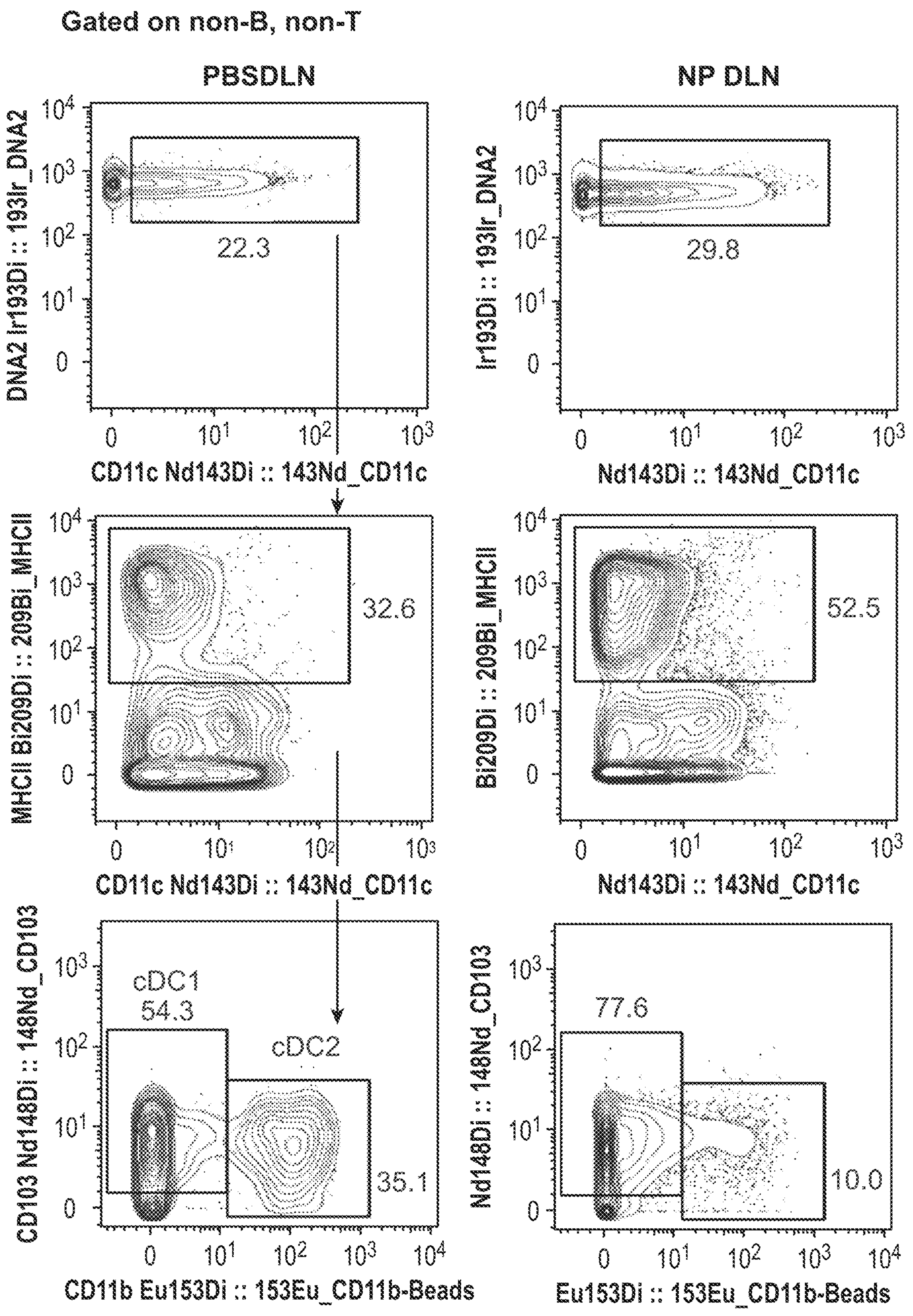
FIG. 8A-8C. TLR7-NPs elicit enhanced immune activation in the tumor draining lymph nodes (dLNs) in MC38 colon cancer model. TLR7-NPs mobilize dendritic cells (DCs) and cells of monocytic lineage in tumor dLNs 3 days post treatment. Representative CyTOF plot (a) and the quantification of cell number (b) of cCD1 and cDC2 DCs. (c) TLR7-NPs elicit a potent CD8 T cell response in tumor dLNs. The representative CyTOF plots of surface activation marker and intracellular staining (Ki67, T-bet, IFNγ, TNFα and Ly6C) of $CD8^+$ T cells from tumor dLNs 3 days post treatment.
Figure 8B:
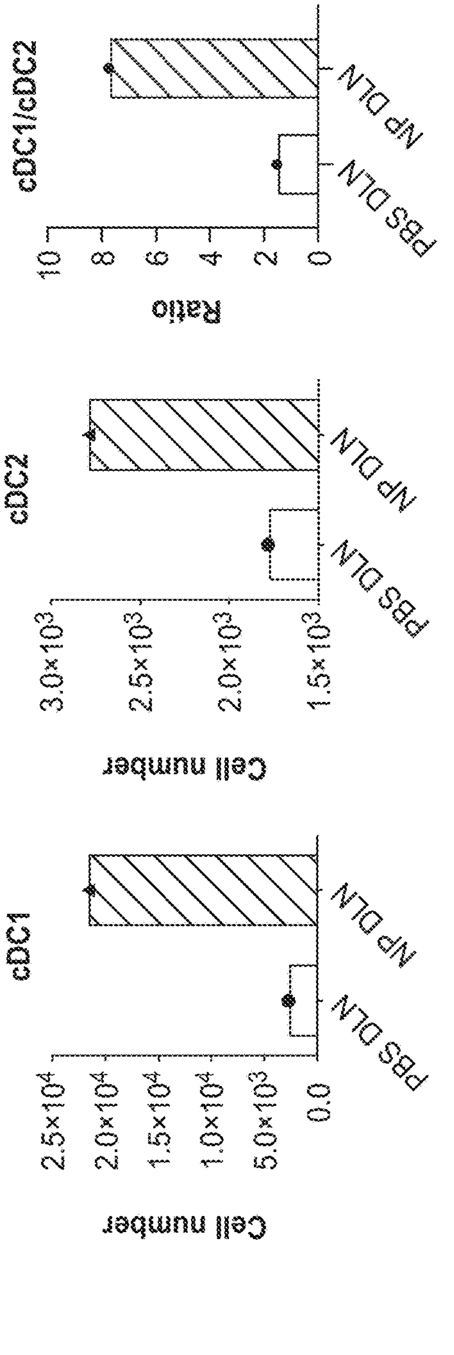
Figure 8C:
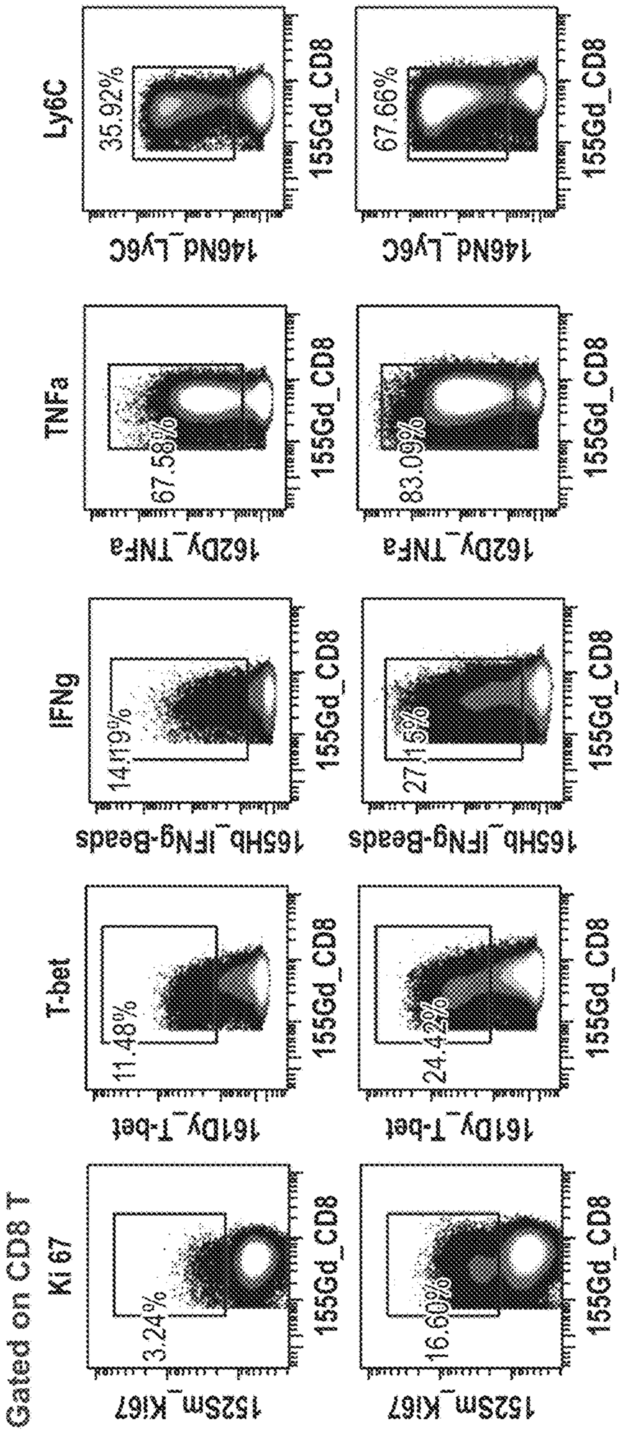

Immune activation within tumor-draining lymph nodes by TLR7-NPs. Tumor draining lymph nodes (DLN) has been suggested of significant importance in initiating a robust anti-tumor response upon immune-modulating therapies. We next used mass cytometry (CyTOF) to evaluate the immune microenvironment changes in the tumor DLN of MC38 tumors three days after TLR7-NP treatment. Results revealed that TLR7-NPs induced a significant increase in both the frequency (FIG. 8A) and the absolute number (FIG. 8B) of cDC1 and cDC2 cells, compared to PBS control. Interestingly, we found TLR7-NPs elicited a higher ratio of cDC1 to cDC2 (FIG. 8B), suggesting TLR7-NPs lead to both the magnitude and the quality of immune responses in tumor DLN. As cDC1s often play a critical role in modulating anti-tumor immunity by capturing, processing, and presenting tumor-antigens on their surface through MHC class I molecules via antigen cross-presentation, we hypothesized that the increased cDC1s by TLR7-NPs would lead to better CD8 T cell activation in the tumor DLN. As expected, a significant up-regulation of Ki67 suggested the proliferation of $CD8^+$ T cells after TLR7-NP treatment (FIG. 8C). In addition, the enhanced IFNγ, Tbet, TNFa, Ly6C expression of $CD8^+$ T cells were also observed in TLR7-NPs treated tumor DLN (FIG. 8C), highlighting the capacity of $CD8^+$ T cells generated by TLR7-NPs to proliferate and activate for antitumor responses.

Figure 9A:
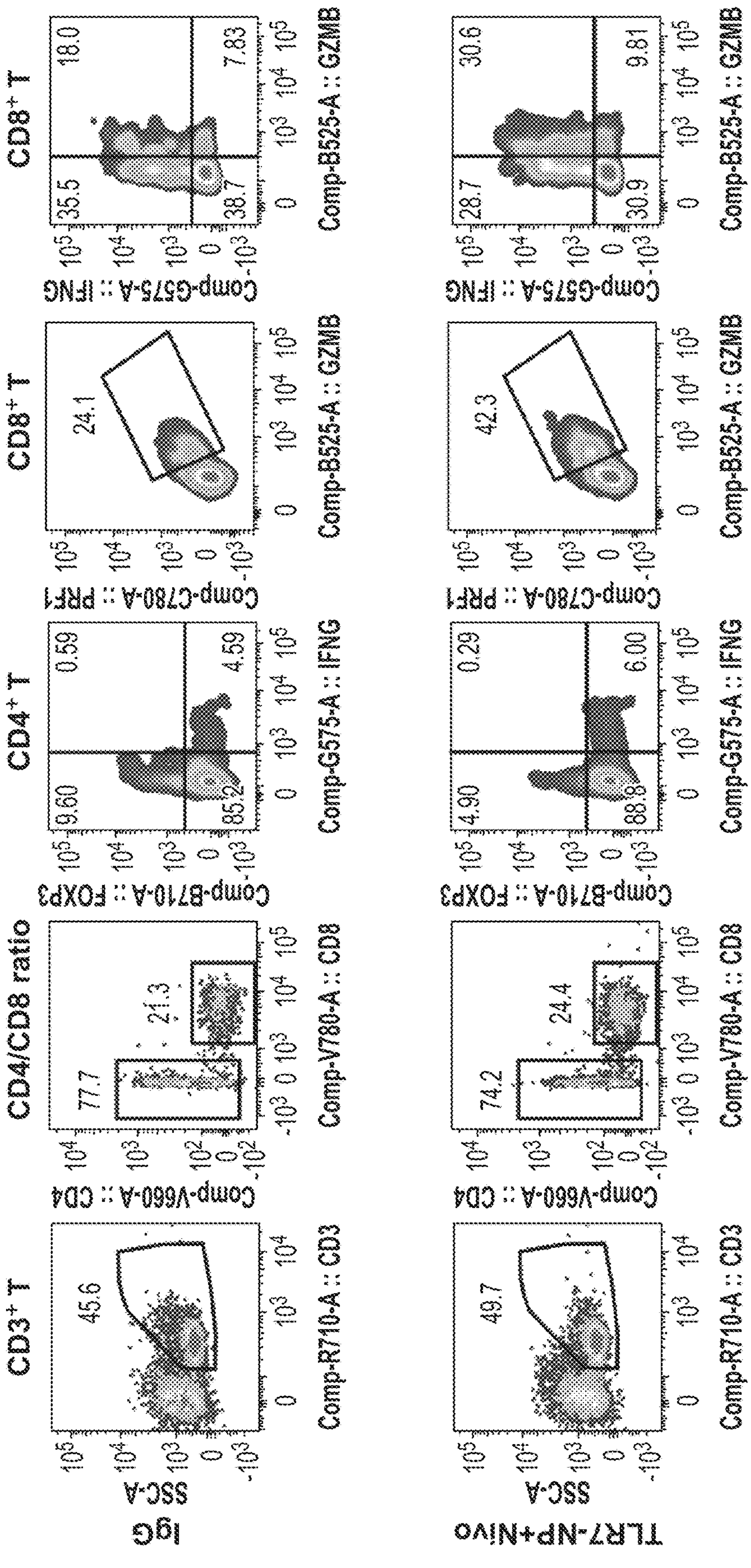
FIG. 9A-9B. Combination therapy of TLR7-NPs and anti-PD-1 checkpoint blockade (nivolumab) enable the robust activation and expansion of endogenous TILs in human skin cancer organoids cocultured with autologous PBMCs. Representative flow cytometry plots (a) and quantification (b) of live $CD3^+$, $CD4^+$, $CD8^+$ TILs and their intracellular staining of FoxP3, IFNγ, PRF1, and Gzmb after treatment.
Figure 9B:
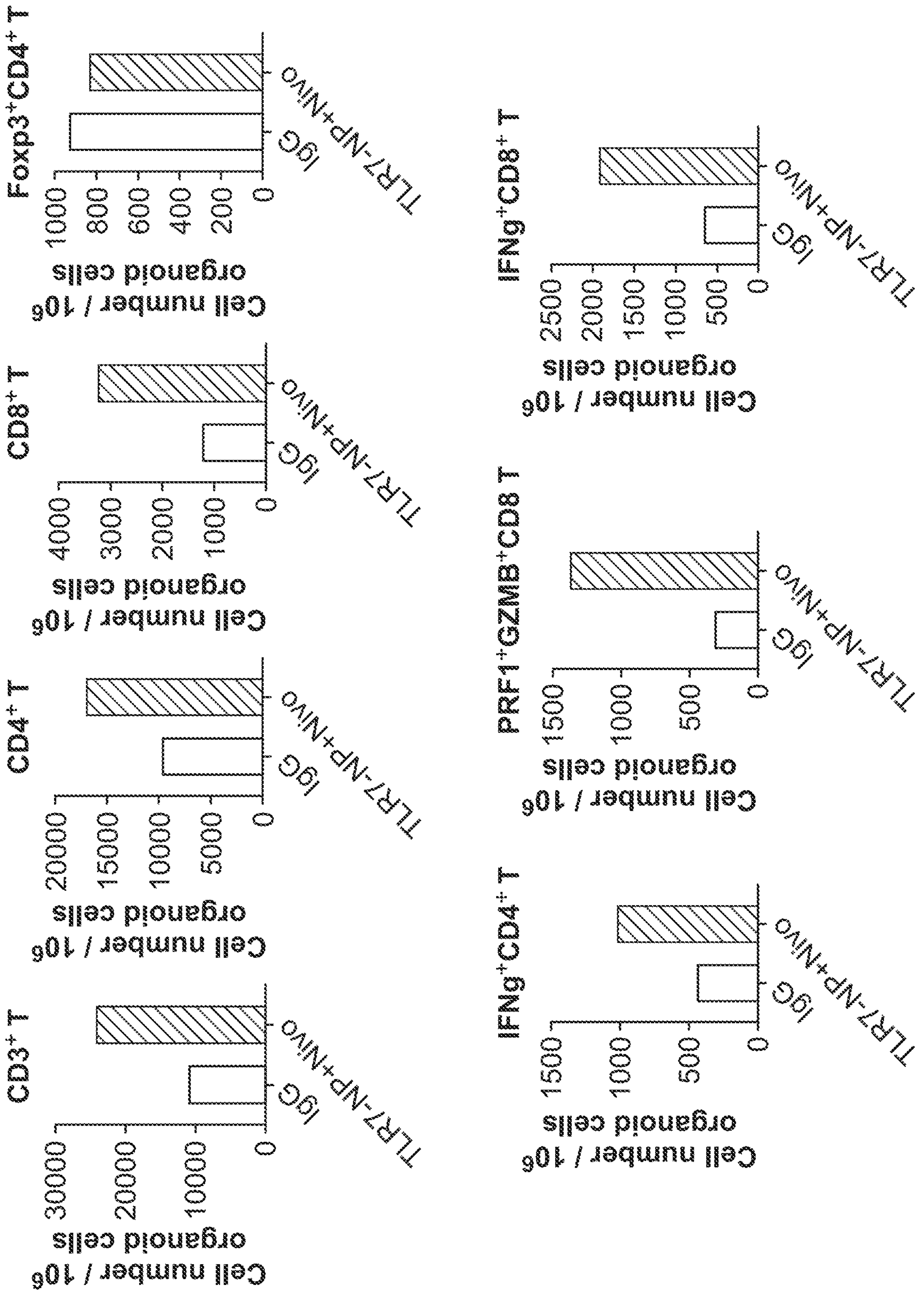

Activation of endogenous human T cells by the combination therapy of TLR7-NPs and anti-PD-1. To investigate the therapeutic potential of this system in human cancer therapy, we then tested the capacity of the combination therapy of TLR7-NPs and anti-PD-1 checkpoint blocking antibody (nivolumab), termed TLR7-NPs+Nivo, to stimulate human T cells in a patient-derived skin tumor organoid cocultured with the autologous PBMCs. The skin tumor organoid generates from human surgically resected tumor biopsies and thus functionally recapitulates the tumor microenvironment and its endogenous infiltrating lymphocytes. After 7 days of continuous co-culture with the organoid and its autologous PBMCs, the combination therapy of TLR7-NPs and Nivo stimulated a robust T cell response, as evidenced by a marked increase in the number of $CD3^+$, $CD4^+$, $CD8^+$ T cells (FIGS. 9A and 9B) compared to a human isotype IgG. Importantly, this combination therapy strongly stimulated both the $CD4^+$ and $CD8^+$ TILs, with strong induction of the T cell effector and cytotoxicity factors Interferon-gamma (IFNγ), Granzyme B (GZMB), and Perforin-1 (PRF1) in these cells (FIG. 9B).

Summary

A new cancer immunotherapeutic modality is provided to elicit potent anti-tumor immune responses without causing undesirable systemic inflammation. Importantly, regardless of any knowledge of tumor antigen, this approach represents a broadly applicable cancer immunotherapeutic strategy. Time-efficient and cost-effective in clinical settings methods are provide, compared to current personalized cancer immunostimulatory development based on discovering patient-specific mutations.

What is claimed is:

1. An immunostimulatory nanoparticle comprising:

a TLR agonist conjugated to a first polymer through a cleavable linkage, precipitated into a nanoparticle;

wherein the first polymer is poly-lactic acid comprising from about 5% to about 25% by weight the TLR agonist.

2. The immunostimulatory nanoparticle of claim 1, wherein the cleavable linkage is an ester linkage.

3. The immunostimulatory nanoparticle of claim 1, wherein the TLR agonist is nano-precipitated with a second polymer.

4. The immunostimulatory nanoparticle of claim 1, wherein the TLR agonist is a TLR7 agonist.

5. The immunostimulatory nanoparticle of claim 1, wherein the TLR agonist is gardiquimod.

6. The immunostimulatory nanoparticle of claim 3, wherein the second polymer comprises polyethylene glycol (PEG) or a conjugate thereof.

7. The immunostimulatory nanoparticle of claim 3, wherein the second polymer comprises PEG conjugated to poly-lactic acid, poly-glycolic acid, or poly(lactic-co-glycolic acid).

8. The immunostimulatory nanoparticle of claim 1, wherein the nanoparticle is from 25 nm to 100 nm in diameter.

9. The immunostimulatory nanoparticle of claim 1, wherein the nanoparticle is from 60 nm to 85 nm in diameter.

10. The immunostimulatory nanoparticle of claim 1, wherein the standard deviation of diameter is less than 25 nm, less than 15 nm, or less than 10 nm.

11. The immunostimulatory nanoparticle of claim 3, further comprising an exogenous tumor antigen that is (i) co-precipitated with the first and second polymers to form the nanoparticle; (ii) conjugated to the adjuvant nanoparticles; or (iii) co-formulated with the nanoparticles in the absence of a physical linkage to the adjuvant nanoparticles.

12. The immunostimulatory nanoparticle of claim 1, wherein the TLR agonist is conjugated to a first polymer through an ester linkage, having the structure:

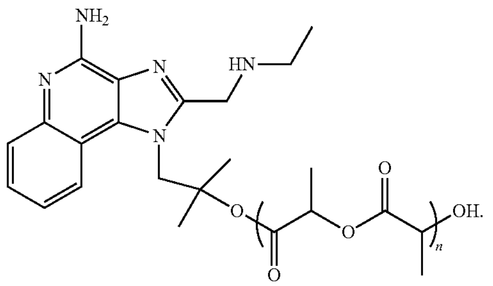

13. A method of treating an individual mammal for cancer, the method comprising:

administering an effective dose of immunostimulatory nanoparticles of claim 1, to activate an immune response against cancer cells present in the individual.

14. The method of claim 13, wherein the immunostimulatory nanoparticles are administered in combination with an effective dose of a second immune regulatory agent.

15. The method of claim 14, wherein the second immune regulatory agent is an immune checkpoint inhibitor of PD-1 or PD-L1, wherein the combination therapy provides for a synergistic response.

16. The method of claim 13, wherein the cancer is a solid tumor, selected from carcinoma, glioma, melanoma, sarcoma, lymphoma, and myeloma.

17. The method of claim 16, wherein the immunostimulatory nanoparticles are administered intra-tumorally.

18. A method of generating a polymer comprising a plurality of ester linked TLR agonist moieties, the method comprising:

initiating a ring-opening polymerization (ROP) reaction of lactide with the TLR agonist as the initiator, to generate a polymer comprising a defined level of TLR agonist loading, wherein the TLR agonist is optionally gardiquimod, wherein the polymer comprises from about 5% to about 25% by weight the TLR agonist.

* * * * *